US011878073B1

(12) United States Patent
Cheuvront et al.

(10) Patent No.: US 11,878,073 B1
(45) Date of Patent: Jan. 23, 2024

(54) GENERATION OF HYDRATION-TARGETED FORMULATIONS AND METHODS OF USE THEREIN

(71) Applicant: ENTRINSIC, LLC, Norwood, MA (US)

(72) Inventors: Samuel N. Cheuvront, Norwood, MA (US); Samantha Niles, Norwood, MA (US); Robert W. Kenefick, Norwood, MA (US)

(73) Assignee: ENTRINSIC, LLC, Norwood, MA (US)

( * ) Notice: Subject to any disclaimer, the term of this patent is extended or adjusted under 35 U.S.C. 154(b) by 0 days.

(21) Appl. No.: 17/933,818

(22) Filed: Sep. 20, 2022

(51) Int. Cl.
*G16H 20/10* (2018.01)
*G16H 20/60* (2018.01)
*A61K 9/00* (2006.01)
*G06N 20/00* (2019.01)
*G16B 40/00* (2019.01)
(Continued)

(52) U.S. Cl.
CPC .......... *A61K 9/0095* (2013.01); *G06N 20/00* (2019.01); *G16B 40/00* (2019.02); *G16B 99/00* (2019.02); *G16H 20/10* (2018.01); *G16H 20/60* (2018.01); *A23L 33/175* (2016.08)

(58) Field of Classification Search
CPC ........ G16H 20/60; G16H 50/30; G16H 10/40; G16H 50/00
See application file for complete search history.

(56) References Cited

U.S. PATENT DOCUMENTS

| 8,993,522 B2 | 3/2015 | Vidyasagar et al. |
| 10,086,007 B2 | 10/2018 | Vidyasagar et al. |
| 10,322,109 B2 | 6/2019 | Vidyasagar et al. |

(Continued)

FOREIGN PATENT DOCUMENTS

| WO | 2012040707 A1 | 3/2012 | |
| WO | WO-2012051591 A2 * | 4/2012 | ........... A23L 33/105 |

(Continued)

OTHER PUBLICATIONS

Millard-Stafford, Mindy, et al. "The beverage hydration index: influence of electrolytes, carbohydrate and protein." Nutrients 13.9 (2021): 2933. (Year: 2021).*

*Primary Examiner* — Jason B Dunham
*Assistant Examiner* — Constantine Siozopoulos
(74) *Attorney, Agent, or Firm* — Greenberg Traurig, LLP

(57) ABSTRACT

At least some embodiments provide illustrative systems and methods that may enable formulation optimization using one or more processor(s) that may be programmed to: receive an amino acid formulation request for an amino acid combination for a hydration beverage, the amino acid formulation request having a first set of optimization criteria including a first water uptake metric for glucose and a taste profile metric associated with a score indicative of an effect on a taste profile of the hydration beverage; access a second set of optimization criteria, including an expression pattern for receptors in the intestine, a second water uptake metric for the amino acid formulation, and amino acid data of each amino acid; and generate an optimized amino acid-based formulation utilizing a hydration beverage optimization engine to optimize a concentration of one or more amino acids based on the first and second sets of optimization criteria.

28 Claims, 10 Drawing Sheets

(51) Int. Cl.
  *G16B 99/00* (2019.01)
  *A23L 33/175* (2016.01)

(56) References Cited

U.S. PATENT DOCUMENTS

| | | |
|---|---|---|
| 10,350,185 B2 | 7/2019 | Vidyasagar et al. |
| 10,758,506 B2 | 9/2020 | Vidyasagar et al. |
| 10,758,507 B2 | 9/2020 | Vidyasagar et al. |
| 10,940,137 B2 | 3/2021 | Vidyasagar et al. |
| 11,357,747 B2 | 6/2022 | Vidyasagar et al. |
| 11,529,325 B2 | 12/2022 | Vidyasagar et al. |
| 11,576,884 B2 | 2/2023 | Vidyasagar et al. |
| 2014/0072679 A1* | 3/2014 | Balassanian ............ A23L 2/52 99/275 |
| 2014/0377374 A1 | 12/2014 | Vidyasagar et al. |
| 2015/0297636 A1 | 10/2015 | Vidyasagar et al. |
| 2017/0156386 A1* | 6/2017 | Baetge ................ A61P 43/00 |
| 2017/0326088 A1 | 11/2017 | Vidyasagar et al. |
| 2019/0000865 A1 | 1/2019 | Vidyasagar et al. |
| 2019/0046504 A1 | 2/2019 | Vidyasagar et al. |
| 2019/0304000 A1* | 10/2019 | Simpson ............... G16B 40/00 |
| 2020/0323820 A1 | 10/2020 | Vidyasagar et al. |
| 2021/0145797 A1 | 5/2021 | Vidyasagar |
| 2021/0196679 A1 | 7/2021 | Vidyasagar et al. |
| 2021/0299076 A1 | 9/2021 | Vidyasagar et al. |
| 2021/0393584 A1 | 12/2021 | Vidyasagar et al. |
| 2022/0016063 A1 | 1/2022 | Vidyasagar et al. |
| 2022/0347143 A1 | 11/2022 | Vidyasagar et al. |
| 2023/0149335 A1 | 5/2023 | Vidyasagar et al. |

FOREIGN PATENT DOCUMENTS

| | | |
|---|---|---|
| WO | 2013119917 A1 | 8/2013 |
| WO | 2013151744 A1 | 3/2014 |
| WO | 2014164736 A1 | 10/2014 |
| WO | 2016085735 A1 | 6/2016 |
| WO | 2018067717 A1 | 4/2018 |
| WO | 2019070750 A1 | 4/2019 |
| WO | 2019070753 A1 | 4/2019 |
| WO | 2019070759 A1 | 4/2019 |
| WO | 2019195594 A1 | 10/2019 |
| WO | 2020092639 A1 | 5/2020 |
| WO | 2020118250 A1 | 6/2020 |
| WO | 2021247652 A1 | 12/2021 |
| WO | 2021243183 A1 | 1/2022 |
| WO | 2022006397 A1 | 1/2022 |

* cited by examiner

GENERATION OF HYDRATION-TARGETED FORMULATIONS AND METHODS OF USE THEREIN

FIELD OF TECHNOLOGY

The present disclosure generally relates to a formulation optimized for hydration when consumed, including a formulation having ingredients optimized for water carrying capacity, and computer-based systems and/or methods for optimization of the hydration formulation.

BACKGROUND OF TECHNOLOGY

Hydration food products, such as beverages, powders, foods, supplements, and others, typically use sugar, such as glucose to augment hydration. The sugar promotes water and electrolyte absorption directly by transcellular uptake (SGLT1) and/or indirectly by transcellular uptake (NHE3). Sugars also promote indirect paracellular uptake of water and electrolytes via solvent drag (SGLT1, GLUT5).

However, sugars may slow gastric emptying, promote net intestinal secretion of fluids, thus slowing the intestinal absorption of fluids, and have other drawbacks including dental carries, weight gain, etc.

SUMMARY OF DESCRIBED SUBJECT MATTER

In some aspects, at least some techniques described herein relate to an illustrative method including: receiving, by a processor, an amino acid formulation request for an amino acid combination for a hydration beverage; where the amino acid formulation request includes a first set of optimization criteria including: a first value of a water uptake metric, the first value being for glucose, a taste profile metric associated with a score indicative of an effect on a taste profile of the hydration beverage, accessing, by the processor, a second set of optimization criteria, including: an expression pattern for at least one associated receptor in the intestine; a second value of the water uptake metric, the second value being for the amino acid formulation, amino acid data including: a plurality of amino acid fixed properties of each amino acid of a plurality of amino acids, where the fixed properties include: an average stoichiometry for each amino acid, and a molecular weight for each amino acid; a plurality of amino acid variable characteristics of each amino acid of a plurality of amino acids, where the variable characteristics include: a molar concentration for each amino acid; generating, by the processor, an optimized amino acid-based formulation including a combination of the one or more amino acids and a concentration of the one or more amino acids by: utilizing a hydration optimization engine to optimize: the combination of one or more amino acids of the plurality of amino acids and the concentration of the one or more amino acids of the plurality of amino acids; where the hydration optimization engine is configured to optimize based at least in part on: the first set of optimization criteria, and the second set of optimization criteria.

In some aspects, at least some techniques described herein relate to an illustrative method, further including: validating, via one or more experimental trials, the optimized amino acid-based formulation for the criteria to obtain validation data indicative of actual performance of the optimized amino acid-based formulation; and retraining the hydration optimization engine based at least in part on the validation data.

In some aspects, at least some techniques described herein relate to an illustrative method, further including: administering the hydration beverage having the optimized amino acid-based formulation for a treatment of a particular disease.

In some aspects, at least some techniques described herein relate to an illustrative method, where the first set of optimization criteria includes cost.

In some aspects, at least some techniques described herein relate to an illustrative method, where the expression pattern includes expression levels of the at least one associated receptor in a plurality of parts of the intestine.

In some aspects, at least some techniques described herein relate to an illustrative method, where the expression pattern includes at least one receptor density and at least one receptor competition metric for the at least one associated receptor.

In some aspects, at least some techniques described herein relate to an illustrative method, where the first set of optimization criteria further includes a total cost associated with the amino acid combination.

In some aspects, at least some techniques described herein relate to an illustrative method, where the amino acid data further includes a cost associated with each amino acid of the plurality of amino acids.

In some aspects, at least some techniques described herein relate to an illustrative method, where the cost of each amino acid includes a cost-per-gram.

In some aspects, at least some techniques described herein relate to an illustrative method, where the amino acid data further includes a taste profile effect metric associated with each amino acid; and where taste profile effect metric includes a sub-score indicative of an individual effect on the taste profile of the hydration beverage of each amino acid.

In some aspects, at least some techniques described herein relate to an illustrative system including; a processor in communication with at least one non-transitory computer readable medium storing software instructions, where the processor may be configured, upon execution of the software instructions, to: receiving, by a processor, an amino acid formulation request for an amino acid combination for a hydration beverage; where the amino acid formulation request includes a first set of optimization criteria: a first value of a water uptake metric, the first value being for glucose, a taste profile metric associated with a score indicative of an effect on a taste profile of the hydration beverage, access a second set of optimization criteria, including: an expression pattern for at least one associated receptor in the intestine; a second value of the water uptake metric, the second value being for the amino acid formulation, amino acid data including a plurality of amino acid characteristics of each amino acid of a plurality of amino acids, where the amino acid data includes: an average stoichiometry for each amino acid, a molecular weight for each amino acid, or a molar concentration for each amino acid; generate an optimized amino acid-based formulation including a combination of the one or more amino acids and a concentration of the one or more amino acids by: utilizing a hydration beverage optimization engine to optimize: the combination of one or more amino acids of the plurality of amino acids and the concentration of the one or more amino acids of the plurality of amino acids; where the hydration beverage optimization engine may be configured to optimize based at least in part on: the first set of optimization criteria, and the second set of optimization criteria.

In some aspects, at least some techniques described herein relate to an illustrative system, where the processor may be further configured to: validating, via one or more experimental trials, the optimized amino acid-based formulation for the criteria.

In some aspects, at least some techniques described herein relate to an illustrative system, where the processor may be further configured to: administering the hydration beverage having the optimized amino acid-based formulation for a treatment of a particular disease.

In some aspects, at least some techniques described herein relate to an illustrative system, where the first set of optimization criteria includes cost.

In some aspects, at least some techniques described herein relate to an illustrative system, where the expression pattern includes expression levels of the at least one associated receptor in the intestine.

In some aspects, at least some techniques described herein relate to an illustrative system, where the expression pattern includes at least one receptor density and at least one receptor competition metric for the at least one associated receptor.

In some aspects, at least some techniques described herein relate to an illustrative system, where the first set of optimization criteria further includes a total cost associated with the amino acid combination.

In some aspects, at least some techniques described herein relate to an illustrative system, where the amino acid data further includes a cost associated with each amino acid of the plurality of amino acids.

In some aspects, at least some techniques described herein relate to an illustrative system, where the cost of each amino acid includes a cost-per-gram.

In some aspects, at least some techniques described herein relate to an illustrative system, where the amino acid data further includes a taste profile effect metric associated with each amino acid; and where taste profile effect metric includes a sub-score indicative of an individual effect on the taste profile of the hydration beverage of each amino acid.

BRIEF DESCRIPTION OF THE DRAWINGS

Various embodiments of the present disclosure may be further explained with reference to the attached drawings, wherein like structures are referred to by like numerals throughout the several views. The drawings shown are not necessarily to scale, with emphasis instead generally being placed upon illustrate the principles of the present disclosure. Therefore, specific structural and functional details disclosed herein are not to be interpreted as limiting, but merely as a representative basis for teaching one skilled in the art to variously employ one or more illustrative embodiments.

FIG. 5 includes a bar graph indicative of transporter expression levels (a) in the duodenum, (b) in the jejunum, and (c) in the ileum.

DETAILED DESCRIPTION

Figure 1:
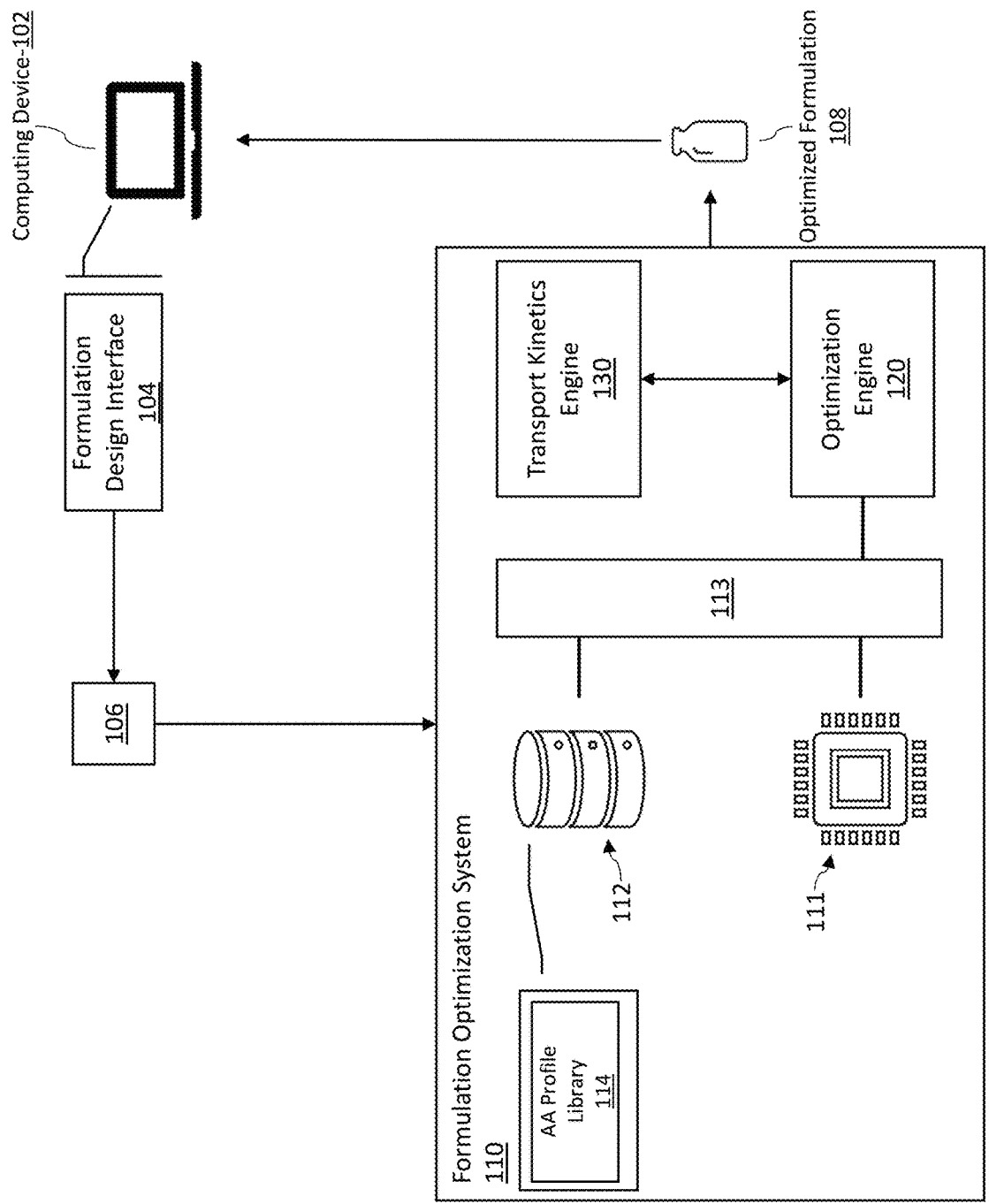
FIG. 1 is a block diagram of an exemplary computer-based system for optimization of a hydration formulation in accordance with one or more embodiments of the present disclosure.

Various detailed embodiments of the present disclosure, taken in conjunction with the accompanying FIGs., are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

FIGS. 1 through 10 illustrate systems and methods of optimizing an amino acid-based hydration formulation for food consumption that improves on water and electrolyte absorption over sugar alone. The following embodiments provide technical solutions and technical improvements that overcome technical problems, drawbacks and/or deficiencies in the technical fields involving identifying optimized combinations of ingredients for a hydration formulation and producing a hydration formulation that improves over sugar-based formulas. For example, there are twenty canonical amino acids with varying transporters, stoichiometry, cost, and transporter regulation characteristics, which results in trillions of possible combinations, each having a different cost, concentration and water carrying capacity profile. No single equation exists to optimize the combination and the number of combinations too high to perform with conventional analytical means. As explained in more detail, below, technical solutions and technical improvements herein include aspects of an improved particular manufacture optimized for hydration upon consumption, a method for treating particular conditions via an optimized hydration formulation, and efficient computer-based optimization of an optimized hydration formulation that implements constraints, requirements, and optimization techniques to identify an optimal formulation for a particular request. Based on such technical features, further technical benefits become available to users and operators of these systems and methods. Moreover, various practical applications of the disclosed technology are also described, which provide further practical benefits to users and operators that are also new and useful improvements in the art.

FIG. 1 is a block diagram of an exemplary computer-based system for optimization of a hydration formulation in accordance with one or more embodiments of the present disclosure.

In some embodiments, to identify an optimal formulation for a hydration substance, a formulation optimization system 110 may be configured with a transport kinetics engine 130 and a hydration optimization engine 120 that uses optimization criteria and amino acid information to produce an optimal formulation based on a request from a user. In some embodiments, the amino acid information may be stored in amino acid profiles of an amino acid profile library 114 in a data store 112.

In some embodiments, the amino acids may include twenty canonical amino acids. For example, the amino acids may include, e.g., Alanine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine, and Valine. In some embodiments, each amino acid may map to a particular transporter in the intestine (see, FIG. 4 and FIG. 5).

In some embodiments, the formulation optimization system 110 may include hardware components such as a processor 111, which may include local or remote processing components. In some embodiments, the processor 111 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor 111 may include data-processing capacity provided by the microprocessor. In some embodiments, the microprocessor may include memory, processing, interface resources, controllers, and counters. In some embodiments, the microprocessor may also include one or more programs stored in memory.

Similarly, the formulation optimization system 110 may include data store 112, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the data store 112 may include, e.g., a suitable non-transient computer readable medium such as, e.g., random access memory (RAM), read only memory (ROM), one or more buffers and/or caches, among other memory devices or any combination thereof.

In some embodiments, the formulation optimization system 110 may implement computer engines for analysis of transport kinetics and carrier competition, and for optimization of a formulation. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational score, power levels, heat tolerances, processing cycle budget, input data scores, output data scores, memory resources, data bus speeds and other design or performance constraints.

In some embodiments, the hydration optimization engine 120 may implement an optimization model configured to leverage characteristics of each amino acid and transporter expression to optimize a formulation of amino acids against a set of requirements. In order to implement the hydration optimization engine 120, the hydration optimization engine 120 may include dedicated and/or shared software components, hardware components, or a combination thereof. For example, the hydration optimization engine 120 may include a dedicated processor and storage. However, in some embodiments, the hydration optimization engine 120 may share hardware resources, including the processor 111 and data store 112 of the formulation optimization system 110 via, e.g., a bus 113. Thus, the hydration optimization engine 120 may include a memory including software and software instructions, such as, e.g., machine learning models and/or logic for optimizing the characteristics of a hydration formulation based on a library of amino acid profiles.

In some embodiments, the hydration optimization engine 120 may utilize carrier competition data associated with the amino acids to optimize a combination of amino acids and amino acid quantities. Amino acids may utilize common transporters in the intestine to carry water via direct and/or indirect transcellular uptake. Saturation of a particular transporter may reduce the effectiveness of additional quantity of amino acid that utilizes the particular transporter. Thus, the hydration optimization engine 120 may employ a transport kinetics engine 130. The transport kinetics engine 130 may utilize one or more transport kinetic models that analyze and/or simulate transport kinetics, including water uptake capacity and/or carrier competition of the amino acids for any candidate formulation. Thus, the transport kinetics engine 130 may refine one or more metrics associated with a candidate formulation based on the combination and/or quantity of candidate amino acids and the effect such combination and/or quantity has on transport kinetics and transporter expression patterns.

In some embodiments, the formulation optimization system 110 may instantiate the hydration optimization engine 120 and/or the transport kinetics engine 130 in response to an amino acid formulation request 106 provided by a computing device 102 of a user. In some embodiments, the computing device 102 may include at least one personal computer (PC), laptop computer, ultra-laptop computer, tablet, touch pad, portable computer, handheld computer, palmtop computer, personal digital assistant (PDA), cellular telephone, combination cellular telephone/PDA, television, terminal, smart device (e.g., smart phone, smart tablet, or smart television), mobile internet device (MID), messaging device, data communication device, and so forth.

In some embodiments, the computing device 102 employ a formulation design interface 104. The formulation design interface 104 may include a user interface (e.g., a graphical user interface (GUI)), a computer/software interface, a hardware interface, or any combination thereof.

In some embodiments, a software interface may include one or more software computing interface technologies, such as, e.g., Common Object Request Broker Architecture (CORBA), an application programming interface (API) and/or application binary interface (ABI), among others or any combination thereof. In some embodiments, an API and/or ABI defines the kinds of calls or requests that may be made, how to make the calls, the data formats that should be used, the conventions to follow, among other requirements and constraints. An "application programming interface" or "API" may be entirely custom, specific to a component, or designed based on an industry-standard to ensure interoperability to enable modular programming through information hiding, allowing users to use the interface independently of the implementation. In some embodiments, CORBA may normalize the method-call semantics between application objects residing either in the same address-space (application) or in remote address-spaces (same host, or remote host on a network).

In some embodiments, a hardware interface may include one or more hardware computing interface technologies, such as, e.g., Universal Serial Bus (USB), IEEE 1394 (FireWire), Ethernet, Thunderbolt™, Serial ATA (SATA) (including eSATA, SATAe, SATAp, etc.), among others or any suitable combination thereof.

In some embodiments, a user interface may include any suitable structure of display elements displayed on a suitable display device for displaying information and/or data to a user via the display elements. The display device may include devices, such as, e.g., a display panel (e.g., liquid crystal display (LCD), organic light emitting diode (OLED) display, light emitting diode (LED) display, micro-LED, mini-LED, thin-film transistor (TFT) display, twisted nematic (TN) display, quantum dot LED, among others or any combination thereof), an augmented reality (AR) and/or virtual reality (VR) display device, a holographic display device, or any other suitable display device or any combination thereof.

In some embodiments, a graphical user interface may include any suitable user interface that allows the user to interface with the computing device 102 through graphical icons and/or other graphical elements. The graphical elements may include, e.g., graphical widgets, graphical containers and/or other graphical interface elements for organizing and/or displaying information and that enable user interaction via a suitable input device.

In some embodiments, an input device may include any software and/or hardware component providing a means for a user to interact with the user interface. The input device may include, e.g., a keyboard, a mouse, a trackpad, a touch-sensitive display, voice input and language processing (e.g., natural language processing (NLP)), motion sensing device (e.g., accelerometer, gyroscope, proximity sensor, radar sensor, camera, etc.), among other input devices and/or any combination thereof.

In some embodiments, the amino acid formulation request 106 may include requirements for a formulation type of an amino acid formulation, such as, e.g., a combination of amino acids for a hydration beverage, for ingredients in a solid or semi-solid food product, or other edible material. In some embodiments, the requirements may include any suitable minimum and/or maximum thresholds of metrics including, e.g., total cost of the formulation, amino acid formulation performance (according to a suitable performance metric), taste profile (e.g., flavor), concentration, quantity of amino acids and/or each amino acid, number of amino acids in the combination, solubility and/or a solubility metric/performance, among others or any combination thereof.

In some embodiments, the amino acid formulation may include any suitable form for an amino acid-based product. For example, the amino acid-based product may include a soluble powder including the amino acid formulation, a solid food product having the amino acid formulation as an ingredient(s), a liquid food product having the amino acid formulation dissolved therein, a liquid and/or gel supplement having the amino acid formulation dissolved therein, or any other suitable amino acid-based product for carrying and/or administering the amino acid formulation.

In some embodiments, the amino acid formulation performance may include a metric indicative of the combination's performance in achieving a particular physiological benefit. For example, the amino acid formulation may be targeted at hydration (e.g., in a beverage), and the performance may be measured according to water uptake via direct transcellular uptake (e.g., using SGLT1), water uptake via indirect transcellular uptake (e.g., using NHE3), water carrier capacity, sodium (Na), a promotion of indirect paracellular uptake of water and/or electrolytes (e.g., using SGLT1, GLUT4, etc.) (e.g., sodium (Na), potassium (K), among others or any combination thereof), promotion and/or inhibition of gastric emptying, among other indicators by which the ability of the combination to maintain hydration may be measured or any combination thereof. In some embodiments, for example, the metric for performance may be measured as a water uptake relative to a competing solution, such as, e.g., a glucose-based formulation. Such a performance metric may have requirements, either predetermined or selectable or both, such as, e.g., a relative water uptake relative to the glucose-based formulation of between, e.g., 1 and 2, 1 and 3, 1 and 4, 1 and 5, 1 and 6, 1 and 7, 1 and 8, 1 and 9, 1 and 10, 2 and 3, 2 and 4, 2 and 5, 2 and 6, 2 and 7, 2 and 8, 2 and 9, 2 and 10, 3 and 4, 3 and 5, 3 and 6, 3 and 7, 3 and 8, 3 and 9, 3 and 10, 4 and 5, 4 and 6, 4 and 7, 4 and 8, 4 and 9, 4 and 10, 5 and 6, 5 and 7, 5 and 8, 5 and 9, 5 and 10, 6 and 7, 6 and 8, 6 and 9, 6 and 10, 7 and 8, 7 and 9, 7 and 10, 8 and 9, 8 and 10, 9 and 10, or other suitable range or any combination thereof.

In some embodiments, the metric may be an absolute performance measure of water uptake. For example, the performance metric may include requirements, either predetermined or selectable or both, such as, e.g., a minimum water uptake capacity, maximum water uptake capacity, or range of water uptake capacity, e.g., 100 and 200 ml, 100 and 300 ml, 100 and 400 ml, 100 and 500 ml, 100 and 600 ml, 100 and 700 ml, 100 and 800 ml, 100 and 900 ml, 100 and 1000 ml, 200 and 300 ml, 200 and 400 ml, 200 and 500 ml, 200 and 600 ml, 200 and 700 ml, 200 and 800 ml, 200 and 900 ml, 200 and 1000 ml, 300 and 400 ml, 300 and 500 ml, 300 and 600 ml, 300 and 700 ml, 300 and 800 ml, 300 and 900 ml, 300 and 10 ml, 400 and 500 ml, 400 and 600 ml, 400 and 700 ml, 400 and 800 ml, 400 and 900 ml, 400 and 1000 ml, 500 and 600 ml, 500 and 700 ml, 500 and 800 ml, 500 and 900 ml, 500 and 1000 ml, 600 and 700 ml, 600 and 800 ml, 600 and 900 ml, 600 and 1000 ml, 700 and 800 ml, 700 and 900 ml, 700 and 1000 ml, 800 and 900 ml, 800 and 1000 ml, 900 and 1000 ml, or other suitable range or any combination thereof.

In some embodiments, the flavor and/or taste profile requirement may be characterized by a quantification of a taste profile of each amino acid in a combination and/or of the combination of amino acids. The quantification may be formed via measurement of human gustatory responses elicited by aqueous solution of each amino acid; taste of D-enantiomers; user provided taste scores of intensities of total taste, sweetness, saltiness, sourness, bitterness and/or umami (e.g., using a category-ratio scale, labeled magnitude scale or other suitable scale); or by any other suitable measurement or any combination thereof. Such a profile measurement may be found in Kawai M, et al. Gustatory sensation of L- and D-amino acids in humans. Amino Acids. 43:2349-2358, 2012, which is incorporated herein by reference in its entirety for all purposes.

In some embodiments, the measurements for taste profile may be generated through study with multiple subjects trained to provide a taste score of the intensity of each quality of taste according to the scale using suprathreshold solutions representing each basic taste or a mixture of tastes. Before sessions for evaluating taste profile of amino acids, subjects experience the evaluation of each taste quality of single or mixture solutions (e.g., various concentrations of NaCl solutions, NaCl plus sucrose-mixed solutions) using the scale repeatedly. In some embodiments, for example, the subjects may score the NaCl solution with a taste score near "moderate" on the scale, and thus the NaCl solution may be provided to the subjects as the reference for "moderate" in total taste intensity at the start of every session.

In some embodiments, three or more geometrically progressive concentrations, e.g., low (L), medium (M), and high (H), for each amino acid may be determined, e.g., by two or three or more trained subjects before the sessions. In some embodiments, the range of concentration may be set so that total taste intensity may be stronger than "weak" and weaker than "strong" on the scale to avoid the range sub-threshold or over sensationally saturated concentration.

In some embodiments, solutions and ultrapure water for a mouth rinse may be kept at room temperature, e.g., 20-25 C, and may be presented to the subjects. In some embodiments, a suitable volume of the solution, e.g., 10 ml, 20 ml, 30 ml, 40 ml, 50 ml 60 ml or other volume of each solution may be served in a tasteless vessel (e.g., a plastic or glass cup). In some embodiments, after rinsing the mouth with water, subjects may sip each amino acid solution (e.g., to sip 5, 10 or 15 ml or other sip volume suitable to taste the solution), taste the solution, and then spit it out. In some embodiments, to reduce the effects of odor on taste scores, subjects may wear nose clips during the tasting. In some embodiments, subjects may be asked to taste score the intensity of each taste quality, total taste, sweetness, saltiness, sourness, bitterness, and umami, using the scale of 100 mm in length. In some embodiments, oral sensation, which may not be ascribed to basic tastes, may also be evaluated as other taste (other taste). The relative position of each descriptor, "barely detectable (BD)", "weak (W)", "moderate (Mod)", "strong (S)", "very strong (VS)" and "strongest imaginably (SI)", may be the same as that of the original the scale. Subjects may be allowed to taste repeatedly after the mouth rinse until all taste qualities may be scored according to the taste score. In some embodiments, solutions of 2 or 3 amino acids (6-9 solutions) may be presented in one session. In some embodiments, the order of presentation of L- or D-amino acids may be randomized.

In some embodiments, labeled magnitude scale scores representative of the taste scores may be transformed into logarithmic values after zero ("no sensation") may be replaced with a small number, e.g., "0.01" or other suitable number to indicate a trivial but non-zero taste. Average and standard error may be calculated using logarithmic values for the intensity of total taste, sweetness, saltiness, sourness, bitterness, umami, and other taste. In some embodiments, Stevens' law may be applied to relate concentration and total taste intensity. In some embodiments, the goodness of fit of the linear regression may be evaluated by one-way ANOVA. In some embodiments, the concentration at Mod-total taste intensity may be calculated according to the psychophysical functions for the comparison of absolute intensity. In some embodiments, the correlation of the slope values or the concentrations at Mod-total taste intensity between L- and D-forms may be evaluated by Spearman's correlation coefficient (r).

In some embodiments, the results may be summarized by the type of amino acids, classified by physicochemical properties, such as, hydrophobicity, size, isoelectric point (pI) and the functional group of the side chain (see, Table 1 of Kawai, et al.). An example of mean intensities of total taste, sweetness, saltiness, sourness, bitterness and umami and other taste of each amino acid solution are summarized in Table 2 of Kawai, et al..

In some embodiments, relationships between log-transformed concentration and total taste intensity for L-amino acids, and for D-amino acids, may be determined using the regression lines of Stevens' psychophysical function. In some embodiments, the main effect of the regression may be highly significant, except for Cys, Lys, Arg and D-Arg (p\0.05). Illustrative slope value and estimated concentration at Mod-total taste intensity are summarized in Table 3 of Kawai, et al..

In some embodiments, the order of mean ranks of slope value of psychophysical functions for L-amino acids may be types III, I, II, VII, V, VI, IV. For D-amino acids, the order may be types VII, I, V, II, III, IV, VI. In the example values, no correlation may be noted for slope values between L- and D-amino acids [r=0.314 (p=0.240)]. In particular, for example, in some embodiments, the difference in slope between L- and D-amino acids may be substantial when their dominant quality of taste is different, as observed especially in types III and VII; e.g., one enantiomer may be sweetness, while the other may be bitterness. In some embodiments, a relationship may be noted between the predominant taste and the slope value common to L- and D-amino acids, with "bitterness>sweetness>sourness" may be utilized. In some embodiments, various implementations detailed herein may utilize an interpretation that amino acids having the same slope values for Stevens' psychophysical functions may may have apparent multiple concentrations. That is, when amino acids A and B have similar taste quality, the following relationship may hold:

$$f_A(x_A) = f_A(l \times x_B)$$

where $f_A$ is the psychophysical function for amino acid A, $x_A$ is the concentration of amino acid A, and l is a constant.

In some embodiments, however, the observed tendency of the slope may differ from that reported in previous studies. In some embodiments, for example, other studies may report that the slope values for most of the D-amino acids are larger than those for L-amino acids, and no conclusive relationship may be determined between slope values and either structure or taste quality.

In some embodiments, among the sweetness-bitterness amino acids, type VI basic amino acids, Lys, Arg, and D-Arg, may have bitterness and/or sweetness intensities that are weakly dependent on concentration. In some embodiments, however, bitterness intensity of neutralized salts of these basic amino acids may show a strong concentration-dependency (data not shown), suggesting that these bulky side chains might be linked to bitterness taste. Alkaline pH of solution of these basic amino acids may perturb sweetness and/or bitterness taste sensation.

In some embodiments, for any given combination of amino acids, a taste score may be produced using the individual taste scores (taste sub-scores) of each amino acid as detailed above, where the taste score and/or the taste sub-score(s) of each amino acid forms an individual taste profile effect metric representative of an individual effect that a particular individual amino acid has on a taste profile of a formulation and/or food product. For example, the taste sub-scores may be aggregated, e.g., via a sum, average, median, weighted sum, weighted average, weighted median, or other suitable aggregation or any combination thereof. In some embodiments, the taste scores of each taste may be aggregated across amino acids in the combination, and/or the tastes scores of each taste may be aggregate within a combination (e.g., total taste), and then the total taste may be aggregated across the amino acids in the combination.

In some embodiments, for any given combination of amino acids, a solubility score for each amino acid in the combination and/or for the overall combination may be determined. An example of a possible framework for determining solubility may be found in Monera O D, et al. Relationship of sidechain hydrophobicity and α-helical propensity on the stability of the single-stranded amphipathic α-helix. J Peptide Sci. 1: 319-329, 1995 (see also: Amino Acids Reference Chart (sigmaaldrich.com)), which is incorporated herein by reference in its entirety for all purposes. Indeed, each amino acid may exhibit a solubility profile that decreases as the amino acid becomes more positive. Thus, a solubility score for each amino acid may be identified in accordance with Sigma Aldrich normalization of Monera, et al. (1995), as represented in Table 4 below.

TABLE 4

Amino Acid Solubility Scores according to Sigma Aldrich Normalization

| At pH 2A | | At pH 7B | |
|---|---|---|---|
| Very Hydrophobic | | | |
| Leu | 100 | Phe | 100 |
| Ile | 100 | Ile | 99 |
| Phe | 92 | Trp | 97 |
| Trp | 84 | Leu | 97 |
| Val | 79 | Val | 76 |
| Met | 74 | Met | 74 |
| Hydrophobic | | | |
| Cys | 52 | Tyr | 63 |
| Tyr | 49 | Cys | 49 |
| Ala | 47 | Ala | 41 |
| Neutral | | | |
| Thr | 13 | Thr | 13 |
| Glu | 8 | His | 8 |
| Gly | 0 | Gly | 0 |
| Ser | −7 | Ser | −5 |
| Gln | −18 | Gln | −10 |
| Asp | −18 | | |
| Hydrophilic | | | |
| Arg | −26 | Arg | −14 |
| Lys | −37 | Lys | −23 |
| Asn | −41 | Asn | −28 |
| His | −42 | Glu | −31 |
| Pro | −46 | Pro | −46 |
| | | | (used pH 2) |
| | | Asp | −55 |

In some embodiments, in response to the amino acid formulation request 106, the formulation optimization system 110 may instantiate the hydration optimization engine 120. In some embodiments, instantiating the hydration optimization engine 120 may include loading and running one or more software programs, initializing a virtual machine, container and/or sandbox in which the hydration optimization engine 120 runs, accessing remote hardware running the hydration optimization engine 120 (e.g., a cloud service or remote computing system, or other remote hardware or any combination thereof), or any other suitable form of instantiation or any combination thereof.

In some embodiments, the hydration optimization engine 120 may access amino acid data that defines attributes of each amino acid. In some embodiments, the amino acid data may be stored in an amino acid profile associated with each amino acid, and the amino acid profiles are stored in an amino acid profile library 114 of the data store 112. In some embodiments, the amino acid data of each amino acid may be stored as structured data to form the amino acid profile of each amino acid. For example, the amino acid profile may include, e.g., one or more vector(s) storing values of the amino acid data according to predefined indices, one or more matrix(ices) storing values of the amino acid data according to predefined indices, one or more data object(s) representing each value of the amino acid data, one or more relational data object(s) representing each value of the amino acid data, among other suitable data structures for representing the values of the amino acid data according to a predefined structure, or any combination thereof.

In some embodiments, the amino acid data may include characteristics that include fixed properties of each amino acid including, e.g., an average stoichiometry for each amino acid, a molecular weight for each amino acid (MW), a mapping to one or more associated transport receptors (see, FIG. 4), number of molecules per mol, substrate affinity ($K_M$), an individual cost associated with each amino acid, a taste profile effect metric associated with each amino (e.g., as detailed above), a maximal transport score ($V_{Max}$), among other properties of each amino acid or any combination thereof.

In some embodiments, the hydration optimization engine 120 may use the amino acid data of each amino acid profile to manipulate variable characteristics of the amino acids and/or combination of amino acids to optimize a combination of one or more amino acids and concentration of each amino acid in the combination. In some embodiments, the variable characteristics may include, e.g., an individual amino acid concentration for each particular individual amino acid (e.g., a molar concentration, a volumetric concentration, a weight concentration, etc.), an individual performance metric (such as, e.g., a water uptake metric associated with a performance in promoting water uptake) associated with each particular individual amino acid, a selection of whether to include each amino acid in a particular combination, the formulation type, among other variable characteristics or any combination thereof.

In some embodiments, the target performance metric and each individual performance metric may be representative of water carrying capacity, water carrying capacity relative to control, or other suitable measure of hydration performance or any combination thereof. In some embodiments, the control may include any suitable substance or compound associated with a competing or other formulation. For example, in the context of hydration, the control may include glucose. Thus, the target performance metric and/or each individual performance metric may be expressed as performance relative to glucose, such as, e.g., a ratio with the performance metric for glucose as a denominator, as a numerator, as a percent difference, or other suitable expression.

In some embodiments, the performance of each amino acid in a particular combination may depend on the other amino acids in the combination. For example, water carrying capacity is a function of the $V_{Max}$ of the amino acid, $K_M$ for the transporter(s) associated with the amino acid, and carrier competition between the amino acid and other amino acids associated with the same transporter. An apparent substrate affinity ($K_{app}$) for a transporter with respect to the amino acid may be determined based on the carrier competition as determined via transport kinetics models.

In some embodiments, the hydration optimization engine 120 may use the transport kinetics engine 130 to perform transport kinetics modelling to determine the total performance for a formulation based on the transport kinetics of each amino acid in the formulation, e.g., by determining and utilizing the $K_{app}$ for each amino acid based on each other amino acid in the formulation.

In some embodiments, amino acid transport may be described by Michaelis-Menten kinetics after incorporating electrochemical driving forces. As a result, transporter simulations need to follow kinetic and thermodynamic principles. These $K_M$-values and the $V_{Max}$-values derived from the transport analysis were used to simulate amino acid transport in mammalian cells using a number of established principles:

(1) Saturation of the transporter by each of its substrate amino acids (AAi) may follow a binding algorithm:

$$\text{Saturation} = [AA_i]/(K_M + [AA_j]) \qquad \text{Eq. (1);}$$

(2) Competition between substrates may be incorporated by calculation of an apparent $K_M$ for amino acid (i) competing with other amino acid (a) substrates of the transporter:

$$K_{app,i} = K_{M,i}\left(1 + \sum \frac{AA_a}{K_{M,a}}\right); \qquad \text{Eq. (2)}$$

(3) A fractional saturation may be calculated for each amino acid (AAi) using its apparent $K_M$;

(4) Saturation of the transporter by co-transported ions may follow the Hill-equation:

$$\text{Saturation} = ([Ion_i]^n/(K_M{}^n + [Ion_i]^n)) \qquad \text{Eq. (3);}$$

(5) Translocation of a charged complex may be affected by the membrane potential, such that the transport score may be multiplied by $$\beta = e^{\left(-\frac{zF0.5\Delta\psi}{RT}\right)}, \qquad \text{Eq. (4)}$$

when translocation may be favored by the membrane potential and divided by β, when translocation occurs against the membrane potential.

In some embodiments, using the above detailed principles, the transport kinetics engine 130 may create a simulation that determines the performance metric for each amino acid in a formulation based on the $K_{app}$ according to Eq. (1) through (4). Using the performance metric for each amino acid, the performance metric for the overall formulation may be determined.

In some embodiments, the requirements may form a first set of optimization criteria that represents targets that the amino acid formulation may be formulated to achieve. In some embodiments, the amino acid data from the amino acid profile of each amino acid may for a second set of optimization criteria, including, e.g., the expression pattern of transporters with respect to each amino acid, the performance metric of each amino acid and amino acid properties and characteristics. In some embodiments, the expression pattern of transporters may include, e.g., a location(s) within the intestine of a transporter, a receptor density in one or more portions of the transporter, among other expression pattern attributes or any combination thereof.

In some embodiments, the hydration optimization engine 120 may use an optimization model to optimize the combination of amino acids and concentration of each amino acid in the combination according to the first set of optimization criteria and the second set of optimization criteria to produce an optimized amino acid-based formulation 108. In some embodiments, an optimized amino acid-based formulation 108 may include a minimization of a total cost and/or quantity of amino acids while maximizing the performance metric, e.g., within the requirements of the first set of optimization criteria. In some embodiments, the quantity of amino acids may include, e.g., number of amino acids, concentration of each amino acid, weight of amino acids, weight of each amino acid, or other suitable measure of quantity or any combination thereof.

In some embodiments, the optimized amino acid-based formulation 108 may include any food product formulation that employs the combination of amino acids to drive performance at promoting and/or inhibiting one or more physiological effects, such as, e.g., improved hydration. The optimized amino acid-based formulation 108 may include additional compounds, substances and/or ingredients, such as flavorings, sugars, electrolytes, binders, emulsifiers, among others or any combination thereof.

In some embodiments, the hydration optimization engine 120 may use any suitable optimization model to perform the optimization. For example, the hydration optimization engine 120 may use, e.g., grid search, heuristics, machine learning, or any other suitable optimization technique or any combination thereof.

In some embodiments, the optimization technique may include a grid search. Accordingly, the hydration optimization engine 120 may use a grid generator to create candidate formulations and populate a grid with the resulting output records and/or metrics thereof. In some embodiments, the combination may include a combination to one feature, to a combination of features or to all of the features. In some embodiments, the hydration optimization engine 120 may produce a set of candidate formulations by iteratively generate combinations of amino acids and amino acid quantities, where each combination defines a new candidate formulation characterized by a unique combination of quantities of amino acids. In some embodiments, each successive combination in the sequence of combinations may be predefined according to, e.g., a stepwise sequence that generates at each step a new combination with a variation to a quantity of each of at least one amino acid, where the quantity may be in a range of zero to 10 mM, zero to 11 mM, zero to 12 mM, zero to 13 mM, zero to 14 mM, zero to 15 mM, or more.

In some embodiments, a user and/or administrator may configure the grid generator to use a particular step-size and a particular maximum. In some embodiments, the step size may be, e.g., 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM or other suitable step size to balance precision and computational complexity. The grid generator may then generate a set of entries based on the stepwise generation of combinations until all possible combinations have been generated, each in its own entry in the grid.

In some embodiments, the hydration optimization engine 120 may then identify the optimum combination based on the first set of optimization criteria and the second set of optimization criteria. To do so, the hydration optimization engine 120 may use the quantity of each amino acid in each test combination and determine for each test combination, e.g., the total quantity of amino acids, a cost associated with the test combination, a test combination performance metric based on the transport kinetics and the amino acid performance of each amino acid, a taste profile of the test combination, among other derived characteristics of the test combination or any combination thereof.

In some embodiments, the hydration optimization engine 120 may filter the test combinations based on the first set of optimization criteria. For example, for a specified target performance, cost and/or taste profile, the hydration optimization engine 120 may identify all entries that represent a combination with derived characteristics that fall outside of the specified target performance, cost and/or taste profile. The filtering of the entries reduces the total number of entries to be analyzed and thus reduces memory footprint and processing needs to conduct the optimization.

In some embodiments, the filtering may be structured in a hierarchical, tiered or nested approach where the test combinations are filtered first by a highest priority optimization criteria, and then by a next highest priority optimization criteria, and so on until the test combinations are filtered by a final, lowest priority optimization criteria. Alternatively, the ordering of the optimization criteria for filtering may be determined as a function of a greatest to least restrictive filtering (e.g., a potential to filter out a greatest number of test combinations to a least number of test combinations), or by any other suitable filtering sequence.

In some embodiments, an example tiering of filters may include, e.g., a first filtering of the test combinations according to performance. For example, a highest priority subset of test combinations may be identified, e.g., according to a number of the highest performing test combinations (e.g., 1, 3, 5, 10, 15, 20, 25, 30, 35, 40, 45, 50, 100 or other suitable number), a highest performing percentile (e.g., $90^{th}$ percentile, $95^{th}$ percentile, $96^{th}$ percentile, $97^{th}$ percentile, $98^{th}$ percentile, $99^{th}$ percentile, $99.5^{th}$ percentile, $99.9^{th}$ percentile, or other suitable percentile of test combinations), test combinations having performance within predetermined thresholds (e.g., between 1 and 3, 1.0 and 3.0, 1.00 and 3.00, or other suitable range, as defined by the formulation request 106, or any combination thereof), or by any other suitable performance filtering criteria.

In some embodiments, the example tiering of filters may include, e.g., a second filtering of the test combinations according to taste profile. For example, a second highest priority subset of test combinations within the subset produced by the first filtering may be identified, e.g., according to a number of the lowest taste intensity test combinations (e.g., 1, 3, 5, 10, 15, 20, 25, 30, 35, 40, 45, 50, 100 or other suitable number), a lowest taste intensity percentile (e.g., $10^{th}$ percentile, $5^{th}$ percentile, $4^{th}$ percentile, $3^{rd}$ percentile, $2^{nd}$ percentile, $1^{st}$ percentile, $0.5^{th}$ percentile, $0.1^{st}$ percentile, or other suitable percentile of test combinations), test combinations having taste intensity within predetermined thresholds (e.g., as defined by the formulation request 106), or by any other suitable taste intensity filtering criteria.

In some embodiments, the example tiering of filters may include, e.g., a third filtering of the test combinations according to total cost of the test combination. For example, a third highest priority subset of test combinations within the subset produced by the first and second filtering may be identified, e.g., according to a number of the lowest cost test combinations (e.g., 1, 3, 5, 10, 15, 20, 25, 30, 35, 40, 45, 50, 100 or other suitable number), a lowest cost percentile (e.g., $10^{th}$ percentile, $5^{th}$ percentile, $4^{th}$ percentile, $3^{rd}$ percentile, $2^{nd}$ percentile, $1^{st}$ percentile, $0.5^{th}$ percentile, $0.1^{th}$ percentile, or other suitable percentile of test combinations), test combinations having cost within predetermined thresholds (e.g., as defined by the formulation request 106), or by any other suitable cost filtering criteria.

In some embodiments, the example tiering of filters may include, e.g., a fourth filtering of the test combinations according to total solubility of the test combination. For example, a fourth highest priority subset of test combinations within the subset produced by the first, second and third filtering may be identified, e.g., according to a number of the lowest solubility test combinations (e.g., 1, 3, 5, 10, 15, 20, 25, 30, 35, 40, 45, 50, 100 or other suitable number), a lowest solubility percentile (e.g., $10^{th}$ percentile, $5^{th}$ percentile, $4^{th}$ percentile, $3^{rd}$ percentile, $2^{nd}$ percentile, $1^{st}$ percentile, $0.5^{th}$ percentile, $0.1^{st}$ percentile, or other suitable percentile of test combinations), test combinations having solubility within predetermined thresholds (e.g., as defined by the formulation request 106), or by any other suitable solubility filtering criteria.

In some embodiments, the tiering of filters may be in any other suitable order using one or more of the optimization criteria, requirements and/or constraints on the amino acid formulation. In some embodiments, such an iterative filtering according to tiers of filters may reduce computational requirements to identify an optimized formulation because each iteration reduces the number of test combinations to analyze using a computationally efficient filtering process.

In some embodiments, the hydration optimization engine 120 may utilize an optimization algorithm to identify the entries having an optimization of the derived characteristics. For example, the optimization algorithm may perform a grid search of the entries to identify a highest performing test combination, a lowest cost test combination, an optimal taste profile (e.g., according to the taste profile of the amino acid formulation request 106), or any other suitable optimization or any combination thereof. For example, the optimization algorithm may optimize a weighted sum, weight average, or other suitable aggregation of the derived characteristics.

In some embodiments, the hydration optimization engine 120 may alternatively or additionally employ an optimization function (e.g., loss function or reward function or both). In such embodiments, the optimization function may assess each test combination according to the first set of optimization criteria and the second set of optimization criteria. For example, the hydration optimization engine 120 may use the quantity of each amino acid in the test combination and determine for the test combination, e.g., the total quantity of amino acids, a cost associated with the test combination, a test combination performance metric based on the transport kinetics and the amino acid performance of each amino acid, a taste profile effect as indicated by the taste profile effect metric of the test combination (e.g., via aggregation of taste sub-scores, and/or by other suitable metric(s)), among other derived characteristics of the test combination or any combination thereof. The derived characteristics of the test combination may then be used to produce a next test combination according to the optimization function applied to the derived characteristics.

In some embodiments, the optimization function may apply gradient descent to determine the next test combination. In some embodiments, the optimization function may determine a gradient of the derived characteristics and interactively determine which amino acid quantities of the test combination to vary. In some embodiments, the optimization function may employ a suitable loss function, such as, e.g., projected gradient descent (PGD), Fast Gradient Sign Method (FGSM), stochastic gradient descent, batch gradient descent, mini-batch gradient descent, or other suitable gradient descent technique.

In some embodiments, the hydration optimization engine 120 may alternatively or additionally employ one or more machine learning models, such as, e.g., one or more regression models and/or one or more neural networks, to model a correlation between combinations of amino acids and a resulting performance metric, e.g., based on formulation type and/or the first set of optimization criteria. Accordingly, in some embodiments, the machine learning model(s) may ingest the first set of optimization criteria, the second set of optimization criteria, and model a set of amino acids and variable characteristics of the amino acids against a predicted performance metric. Thus, the machine learning model may treat the variable characteristics, selection of amino acids, and amino acid concentrations as parameters of the optimization algorithm to be trained to achieve the target performance. Alternatively, or in addition, the machine learning model may employ parameters that directly model an optimized amino acid formulation based on the first set of optimization criteria and the second set of optimization criteria.

In some embodiments, the formulation optimization engine 120 may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network.

In some embodiments and, optionally, in combination of any embodiment described above or below, an exemplary implementation of Neural Network may be executed as follows:
  a) define Neural Network architecture/model,
  b) transfer the input data to the exemplary neural network model,
  c) train the exemplary model incrementally,
  d) determine the accuracy for a specific number of timesteps,
  e) apply the exemplary trained model to process the newly-received input data,
  f) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node may be activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

As a result, the hydration optimization engine 120 may identify and output an optimized combination as the optimized amino acid-based formulation 108. In some embodiments, the optimized amino acid-based formulation 108 may be output to the computing device 102 and/or to any other suitable device/system. For example, in some embodiments, the formulation optimization system 110 may communicate the optimized amino acid-based formulation 108 to a manufacturing facility, e.g., via a network connection, or to one or more production equipment, e.g., via a network and/or local connection. The manufacturing facility and the production equipment may be configured to receive the optimized amino acid-based formulation 108 and automatically control equipment such as, e.g., hoppers holding the amino acids, mixing equipment, heating, and cooling equipment, bottling and/or packaging equipment, among other equipment to automatically produce a food product with the optimized amino acid-based formulation.

In some embodiments, the optimized amino acid-based formulation 108 may be received by the computing device 102 and displayed to a user. In some embodiments, the optimized amino acid-based formulation 108 may be displayed via, e.g., the display device as detailed above, via a suitable application and/or webpage, among other hardware and/or software.

In some embodiments, to validate the optimized amino acid-based formulation 108, the user may conduct one or more experimental trials. For example, an experimental trial may be designed that administers a particular quantity of a food product (e.g., beverage) to each subject of a set of enrolled subjects. The enrolled subjects may have two groups, a control group, and a test group. The test group may be administered the food product with the optimized amino acid-based formulation 108 included, and the control group may be administered the food product without the optimized amino acid-based formulation 108 included. In some embodiments, the experimental trial may include administering the food product while the subjects are at rest, exercising, before exercising, after exercising, while undergoing a particular treatment, or any other suitable test scenario for which the optimized amino acid-based formulation 108 may be to be used.

In some embodiments, the experimental trial(s) may produce validation data indicative of the actual performance of the optimized amino acid-based formulation 108. In some embodiments, the actual performance may differ from the projected performance indicated by the performance metric provided by the formulation optimization engine 120. Accordingly, the formulation optimization system 110 may use the validation data as feedback to the formulation optimization engine 120 and/or transport kinetics engine 130 to train parameters of the optimization model(s) and/or the transport kinetics model(s). For example, weights and/or parameters of optimization algorithm may be updated using, e.g., a loss and/or error function, and back propagation of the error using a suitable backpropagation technique. In some embodiments, the loss and/or error function may determine a loss/error between the performance metric of the optimized formulation 108 and the validation data. Accordingly, the loss/error function may include, e.g., mean squared error, likelihood loss, log-likelihood loss (e.g., cross entropy loss), or other suitable loss/error function or any combination thereof. In some embodiments, based on the loss/error, an optimizer algorithm may optimize the weights and/or parameters of the optimization algorithm via, e.g., gradient descent, such as, e.g., projected gradient descent (PGD), Fast Gradient Sign Method (FGSM), stochastic gradient descent, batch gradient descent, mini-batch gradient descent, or other suitable gradient descent technique. Accordingly, the optimization algorithm may be updated based on actual performance metrics to better model an optimized combination of amino acids for particular performance targets based on the amino acid formulation request 106.

In some embodiments, the amino acid formulation request 106 may be associated with a particular disease for which the food product may be designed to treat (e.g., designed according to the first set of optimization criteria). In some embodiments, whether or not an experimental trial is conducted, a food product having the optimized amino acid-based formulation 108 may be administered to treat the disease. For example, conditions involving, e.g., dehydration and/or malnutrition, may benefit from a food product having an amino acid formulation optimized for performance (e.g., water uptake) and/or cost. Thus, the optimized amino acid-based formulation 108 may be administered to patients of the condition to assist in resolving the symptoms of the condition.

Examples of treatments of conditions that may benefit from an administration regimen of an optimized amino acid-based hydration formulation may include, e.g., infectious disease treatment, exertional heat stress treatment, diabetes treatment, gastroenteritis treatment, inflammatory bowel diseases (IBD) treatment, diuretic drug use treatment, among others or any combination thereof. In some embodiments, infectious disease (food poisoning, flu, etc.) that causes vomiting and/or diarrhea may lead to dehydration. Accordingly, an administration regimen may include administration at onset of illness, during the length of illness, and/or during recovery.

In some embodiments, exertional heat stress (dehydration caused by exercise or working in the heat), may benefit from an administration regimen prior to an exertional event, during the exertion, and/or during recovery. In some embodiments, diabetes may result in kidneys excreting excess into the urine, which may drag additional fluid/water with it, leading to dehydration. Accordingly, diabetes treatment may benefit from an administration regimen that may be ad libitum.

Figure 2:
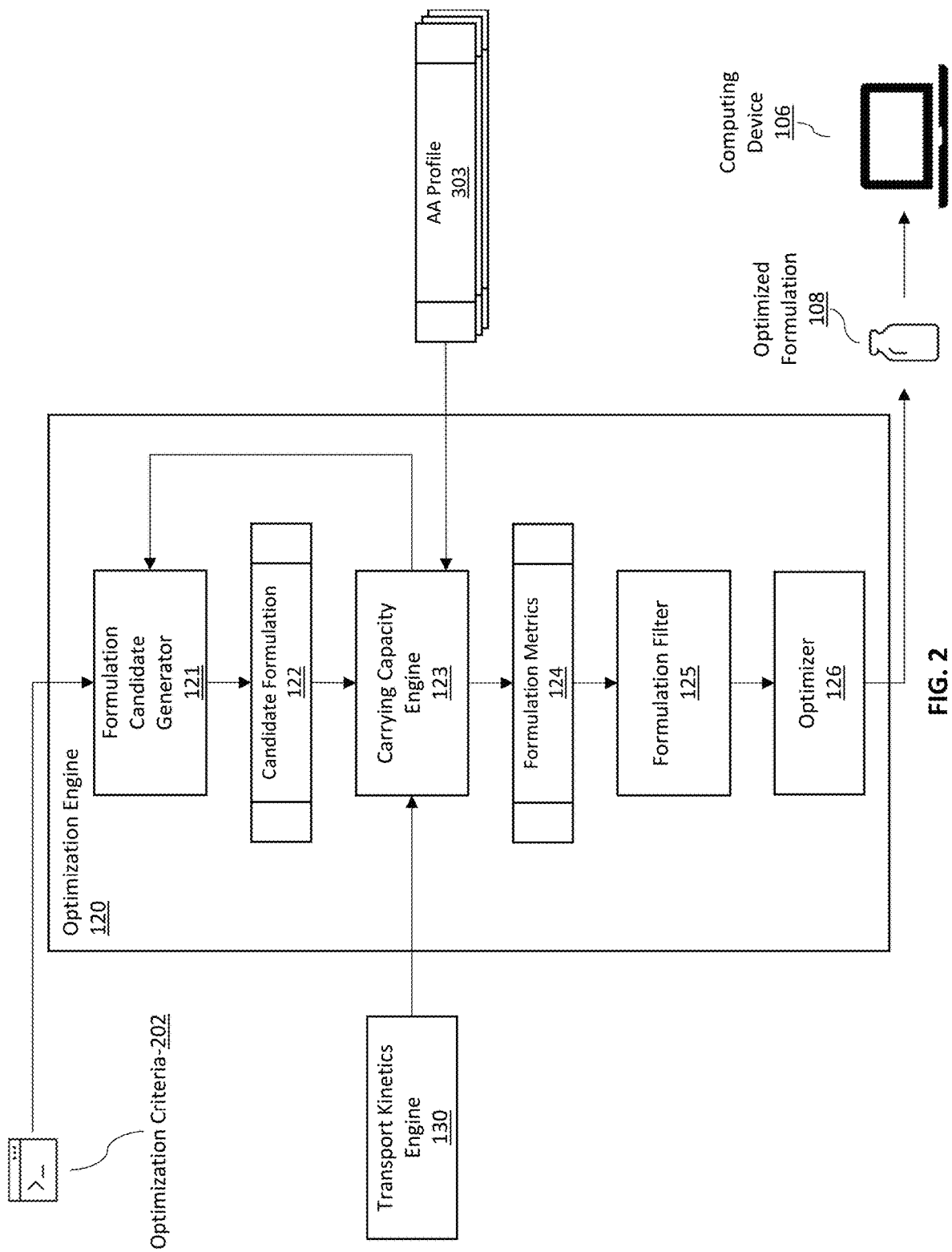
FIG. 2 is a block diagram of a computer-based system for implementing a hydration formulation optimization process to produce an optimized hydration formulation in accordance with one or more embodiments of the present disclosure.

FIG. 2 is a block diagram of a computer-based system for implementing a hydration formulation optimization process to produce an optimized hydration formulation in accordance with one or more embodiments of the present disclosure.

In some embodiments, the hydration optimization engine 120 may receive the first set of optimization criteria 202 from the amino acid formulation request 106. In some embodiments, the first set of optimization criteria 202 may include requirements for an amino acid formulation, such as, e.g., a combination of amino acids for a hydration beverage, for ingredients in a solid or semi-solid food product, or other edible material. In some embodiments, the requirements may include any suitable minimum and/or maximum thresholds of metrics including, e.g., cost, amino acid formulation performance, taste profile (e.g., flavor), concentration, quantity of amino acids and/or each amino acid, number of amino acids in the combination, solubility, among others or any combination thereof.

In some embodiments, the hydration optimization engine 120 may utilize a formulation candidate generator 121 to generate candidate formulations 122. As detailed above, each formulation may include a combination of amino acids with a particular quantity (e.g., concentration for a given volume of liquid such as water) of each amino acid in the combination.

In some embodiments, the formulation candidate generator 121 may reduce resource requirements by establishing initial parameters for all candidate formulations 122. For example, an initial parameter may be to begin with between 1 and 15 millimolar (mM) each of the amino acids. In some embodiments, the choice of mM may be based on the Km saturation kinetics of the amino acids, or it may be based on the summation of amino acids reaching a predetermined upper limit of concentration based upon an estimated ceiling for costs or a lower limit for meaningful hydration superiority when replacing sugar in a beverage, such as oral rehydration solutions or sports drinks. In some embodiments, the predetermined upper limit may be any suitable concentration based on the cost considerations, among other factors, such as, e.g., in a range of 1 to 15 g/L, in a range of 2 to 15 g/L, in a range of 3 to 15 g/L, in a range of 4 to 15 g/L, in a range of 5 to 15 g/L, in a range of 6 to 15 g/L, in a range of 7 to 15 g/L, in a range of 8 to 15 g/L, in a range of 9 to 15 g/L, in a range of 10 to 15 g/L, in a range of 1 to 14 g/L, in a range of 1 to 13 g/L, in a range of 1 to 12 g/L, in a range of 1 to 11 g/L, in a range of 1 to 10 g/L, in a range of 1 to 9 g/L, in a range of 1 to 8 g/L, in a range of 1 to 7 g/L, in a range of 1 to 6 g/L, in a range of 1 to 5 g/L, in a range of 8 to 12 g/L, in a range of 9 to 12 g/L, in a range of 10 to 12 g/L, in a range of 8 to 11 g/L, in a range of 8 to 10 g/L, in a range of 9 to 11 g/L, or other suitable range. In some embodiments, the predetermined upper limit may be, e.g., 10 g/L. From this starting point the superiority of amino acid water transport over that of glucose may be calculated and expressed on a gram-to-gram basis.

Additionally, or alternatively, for example, an initial parameter may be to begin with a particular concentration of a limited set of amino acids. In some embodiments, primary intestinal sodium transport via the NHE3 antiporter might be targeted using amino acids known or suspected to upregulate NHE3. Strategically, any amino acid that stimulates NHE3 and has very high carrier density along all three parts of the small intestine could be targeted for initial formula inclusion. Therefore, combinations of amino acids that stimulate net Na absorption, established via the initial parameters, could always be part of every formula to maximize the potential for primary active transport of Na via NHE3. In some embodiments, amino acids with these characteristics may increase the likelihood that end formulations are superior to glucose not just in calculation, but in practice (e.g., $D_2O$ kinetics).

In some embodiments, to facilitate prioritization of amino acids for subsequent candidate formulations 122, the formulation candidate generator 121 may rank the remaining amino acids based on their average water carrying capacity. The amino acids may then be added in descending order using, e.g., 1 to 15 mM each until you reach no the predetermined upper limit of concentration (as detailed above).

$$MW * \frac{mM}{1000} = g/L \qquad \text{Eq. (5)}$$

In some embodiments, for any of the selected amino acids using carrier proteins SLC1A1 or SLC6A20, each subsequent candidate formulation may increase the selected amino acids to higher concentrations. In some embodiments, the remaining amino acids may be adjusted evenly to lower concentrations until the total gram weight reaches the predetermined upper limit of concentration. In some embodiments, two or fewer amino acids share each of the carriers SLC1A1 or SLC6A20, thus limiting carrier competition.

In some embodiments, each candidate formulation 122 may be provided to a carrying capacity engine 123 to determine the water carrying capacity of each amino acid in the candidate formulation 122 and resulting formulation metrics 124. In some embodiments, the formulation metrics 124 may include a metric indicative of the combination's performance in achieving a particular physiological benefit. For example, the amino acid formulation may be targeted at hydration (e.g., in a beverage), and the performance may be measured according to water uptake via direct transcellular uptake (e.g., using SGLT1), water uptake via indirect transcellular uptake (e.g., using NHE3), water carrier capacity, sodium (Na), a promotion of indirect paracellular uptake of water and/or electrolytes (e.g., using SGLT1, GLUT4, etc.) (e.g., sodium (Na), potassium (K), among others or any combination thereof), promotion and/or inhibition of gastric emptying, among other indicators by which the ability of the combination to maintain hydration may be measured or any combination thereof. In an example embodiment, the performance of the candidate formulation 122 may be measured against the performance of glucose for water uptake when administered in a beverage.

In some embodiments, for each candidate formulation, a carrying capacity engine 123 may calculate the mean symport water carrying capacity of 1 g of each amino acid in the candidate formulation 122, e.g., based on the amino acid data of each amino acid profile associated with each amino acid. For amino acids that use greater than one carrier, the mean Na stoichiometry may be used in the numerator of the calculation, which may be represented below:

$$\frac{1 \text{ g}}{MW} * \left(235 * \frac{Na}{2}\right) * 18 = X \text{ mL}, \qquad \text{Eq. (6)}$$

where MW is molecular weight in g per mol; Na is the stoichiometric ratio of Na to AA (0, 1, 2, or 3) using '2' as the denominator to normalize for glucose stoichiometry. In some embodiments, Eq. (6) denotes secondary active transport potential via symporters such as SGLT1 (SLC5A1) or the amino acid SLC-family of carriers. NHE3 water and electrolyte transport is not a part of Eq. (6) and may be treated as equal among amino acids and glucose based upon work showing similar relative NHE3 expression for glucose versus amino acids in the presence of CT.

In some embodiments, the number of water molecules associated with each mol of substrate is '235' based on the mean of measured values for glucose ranging from 210 to 260. The value '18' represents the volume of water occupied by one mol of water. In some embodiments, amino acids transport on 'average' 235 water molecules per mol also. The rationale for this may be that 50 to 200 water molecules per mol of amino acid have been reported for small numbers of amino acids with limited Na stoichiometry ranges. Indeed, there are twenty canonical amino acids that may use multiple amino acid carriers varying in Na stoichiometry which may be less than, equal to, or greater than glucose.

In some embodiments, for each candidate formulation, a carrying capacity engine 123 may calculate the symport water carrying capacity of 1 g glucose using the equation (6) as:

$$\frac{1 \text{ g}}{180.16} * 235 * 18 = 23.479 \text{ mL}.$$

In some embodiments, using Eq. (6) above, the carrying capacity engine 123 may calculate the mean-weighted MW and Na stoichiometry. In some embodiments, this may provide the fairest way of calculating the potential symport water carrying capacity.

In some embodiments, the transport kinetics engine 130 may instead determine the water carrying capacity. In some embodiments, the transport kinetics engine 130 to perform transport kinetics modelling to determine the performance of each individual amino acid in the candidate formulation 122, and/or the total performance for candidate formulation 122 based on the transport kinetics of each amino acid in the candidate formulation 122, e.g., by determining and utilizing the $K_{app}$ for each amino acid based on each other amino acid in the formulation.

In some embodiments, the transport kinetics engine 130 may create a simulation that determines the performance metric for each amino acid in a formulation based on the $K_{app}$ according to Eq. (1) through (4). Using the performance metric for each amino acid, the performance metric for the overall formulation may be determined.

In some embodiments, a carrying capacity engine 123 may calculate the water carrying capacity of, e.g., 1 g of the candidate formula 122 and compare to glucose expressed as a percentage, e.g., as per the following equation:

$$\frac{\text{amino acid, mL}}{\text{glucose, mL}} * 100. \qquad \text{Eq. (7)}$$

In some embodiments, the target performance of the first set of optimization criteria may be to achieve formulations with a symport water carrying capacity greater than or equal to 150% of glucose, though any other suitable performance criteria may be used, such as, e.g., 100% or more. Successful formulations may have smaller molecular weights and larger Na stoichiometry (on average) than glucose.

In some embodiments, the symport water carrying capacity may be output as formulation metrics 124 that characterize the performance of the candidate formulation 122. In some embodiments, once the formulation metrics 124 for a given candidate formulation 122 are output, the carrying capacity engine 123 may return to the formulation candidate generator 121 to await a next candidate formulation 122. In some embodiments, for the next candidate formulation 122, the formulation candidate generator 121 may iteratively adjust the mM concentrations of the available amino acids by 1 mM increments in as many combinations as possible using prescribed limits. In some embodiments, the prescribed limits may include a range from 0 to 15 mM for each of the 20 canonical amino acids.

In some embodiments, upon outputting formulation metrics 124 for each candidate formulation 122, the optimized amino acid-based formulation 108 may be identified. To do so, the hydration optimization engine 120 may first filter the candidate formulations 122 based on the first set of optimization criteria. For example, for a specified target performance, cost and/or taste profile, the hydration optimization engine 120 may identify all candidate formulations 122 that represent a combination with the formulation metrics 124 that fall outside of the specified target performance, cost and/or taste profile. The filtering of the candidate formulations 122 reduces the total number of entries to be analyzed and thus reduces memory footprint and processing needs to conduct the optimization.

In some embodiments, an optimizer 126 may analyze the remaining candidate formulations 122 to determine an optimized amino acid-based formulation 108. In some embodiments, to do so, the optimizer 126 may simply rank the candidate formulations 122 according to symport water carrying capacity, cost, or a combination thereof. The highest ranked candidate formulation 122 may then be selected as the optimized amino acid-based formulation 108.

In some embodiments, the optimized amino acid-based formulation 108 using a symport water carrying capacity that may be at least 150% that of glucose and that may have a concentration within the predetermined upper limit of concentration may be identified as the formulation of Table 5.

TABLE 5

Optimized amino acid-based formulation

| Example API | Average Stoichiometry | Molecular weight (g/mol) | Molar concentration (mM) | g/L | Price per gram | Cost per g/L weight |
|---|---|---|---|---|---|---|
| Alanine | 0-3 | 80-170 | 0-15 | 0-10 | 0.001-0.1 | 0.001-1 |
| Arginine | 0-3 | 80-170 | 0-15 | 0-10 | 0.001-0.1 | 0.001-1 |
| Asparagine | 0-3 | 80-170 | 0-15 | 0-10 | 0.001-0.1 | 0.001-1 |
| Aspartic acid | 0-3 | 80-170 | 0-15 | 0-10 | 0.001-0.1 | 0.001-1 |
| Cysteine | 0-3 | 80-170 | 0-15 | 0-10 | 0.001-0.1 | 0.001-1 |
| Glutamic acid | 0-3 | 80-170 | 0-15 | 0-10 | 0.001-0.1 | 0.001-1 |
| Glutamine | 0-3 | 80-170 | 0-15 | 0-10 | 0.001-0.1 | 0.001-1 |
| Glycine | 0-3 | 80-170 | 0-15 | 0-10 | 0.001-0.1 | 0.001-1 |
| Histidine | 0-3 | 80-170 | 0-15 | 0-10 | 0.001-0.1 | 0.001-1 |
| Isoleucine | 0-3 | 80-170 | 0-15 | 0-10 | 0.001-0.1 | 0.001-1 |
| Leucine | 0-3 | 80-170 | 0-15 | 0-10 | 0.001-0.1 | 0.001-1 |
| Lysine | 0-3 | 80-170 | 0-15 | 0-10 | 0.001-0.1 | 0.001-1 |
| Methionine | 0-3 | 80-170 | 0-15 | 0-10 | 0.001-0.1 | 0.001-1 |
| Phenylalanine | 0-3 | 80-170 | 0-15 | 0-10 | 0.001-0.1 | 0.001-1 |
| Proline | 0-3 | 80-170 | 0-15 | 0-10 | 0.001-0.1 | 0.001-1 |
| Serine | 0-3 | 80-170 | 0-15 | 0-10 | 0.001-0.1 | 0.001-1 |
| Tyrosine | 0-3 | 80-170 | 0-15 | 0-10 | 0.001-0.1 | 0.001-1 |
| Tryptophan | 0-3 | 80-170 | 0-15 | 0-10 | 0.001-0.1 | 0.001-1 |
| Threonine | 0-3 | 80-170 | 0-15 | 0-10 | 0.001-0.1 | 0.001-1 |
| Valine | 0-3 | 80-170 | 0-15 | 0-10 | 0.001-0.1 | 0.001-1 |
| SUM | 0-3 | 80-250 | 0-300 | 0-10 | 0.001-0.1 | 0.001-1 |
| Glucose | 2.0 | 180.16 | | 0-10 | | |
| GLU mL | | AA mL | | | Greater than 5% | |
| XXX.XX | | XXX.XX | | | 1.0-2.0 | |

Figure 3:
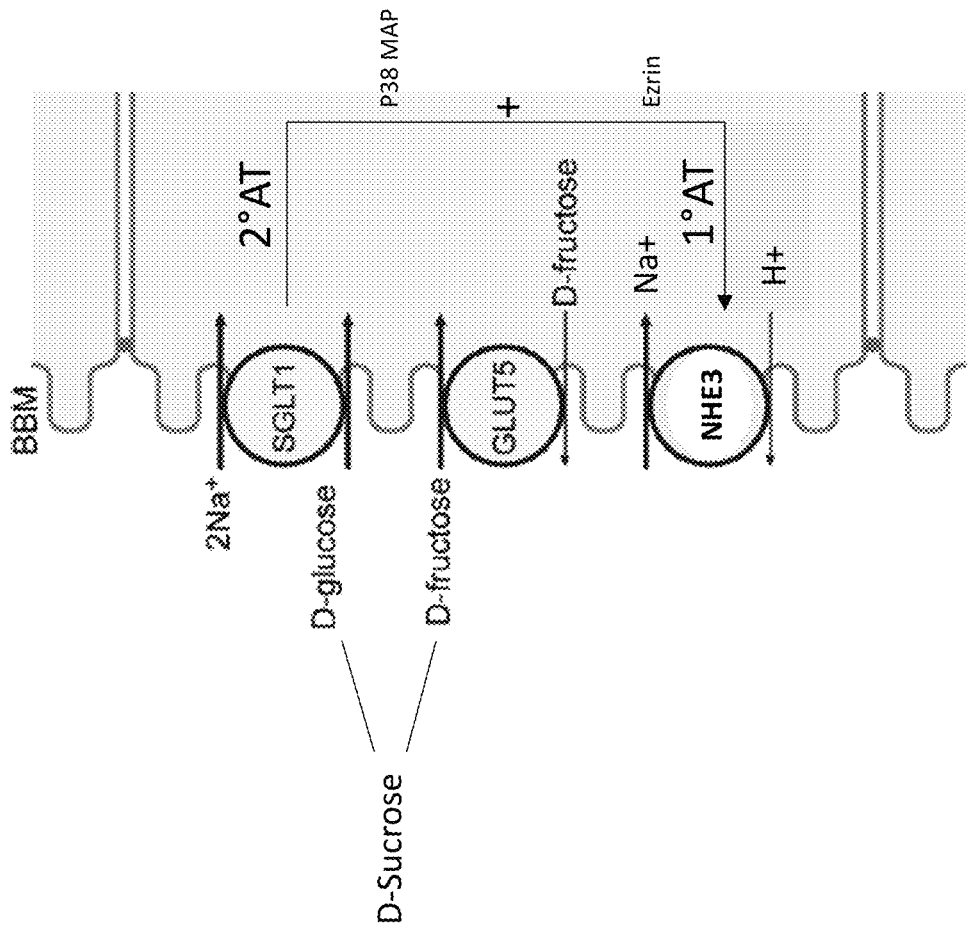
FIG. 3 is an illustration depicting sugar-augmented hydration mechanisms in accordance with one or more embodiments of the present disclosure.

FIG. 3 is an illustration depicting sugar-augmented hydration mechanisms in accordance with one or more embodiments of the present disclosure.

Figure 4:
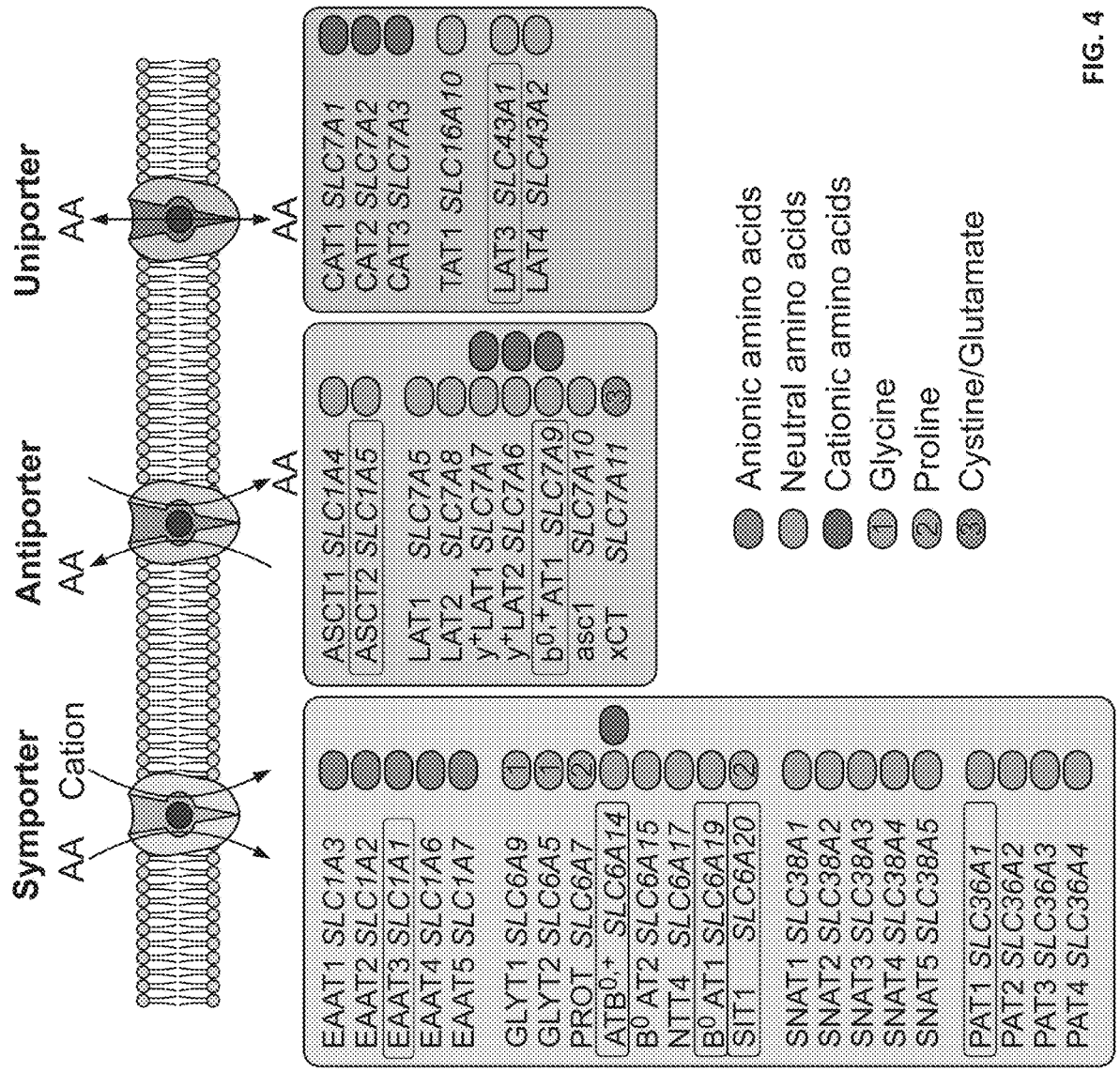
FIG. 4 is an illustration depicting amino acid-augmented hydration mechanisms in accordance with one or more embodiments of the present disclosure.

FIG. 4 is an illustration depicting amino acid-augmented hydration mechanisms in accordance with one or more embodiments of the present disclosure.

Figure 5:
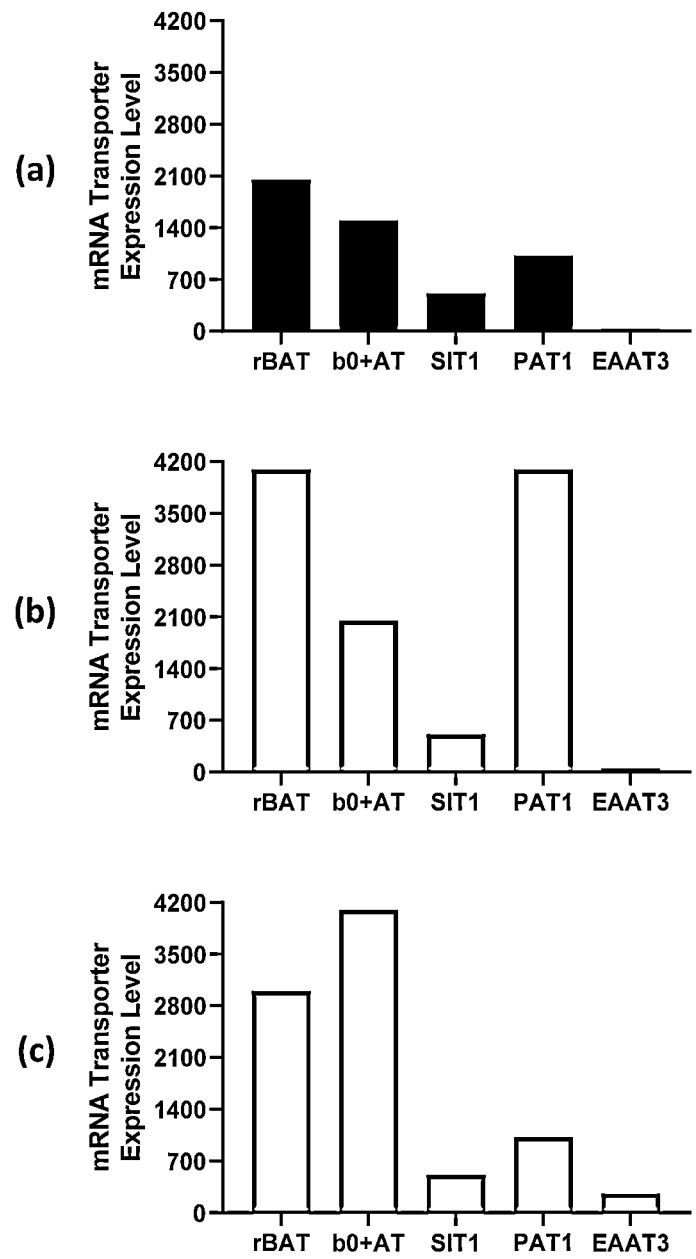
FIG. 5 is an illustration depicting transporter expression levels indicative of transporter location and density in the duodenum, jejunum, and ileum of an intestinal tract in accordance with one or more embodiments of the present disclosure.

FIG. 5 is an illustration depicting transporter expression levels indicative of transporter location and density in the duodenum, jejunum, and ileum of an intestinal tract in accordance with one or more embodiments of the present disclosure. FIG. 5 includes a bar graph indicative of transporter expression levels (a) in the duodenum, (b) in the jejunum, and (c) in the ileum.

Figure 6:
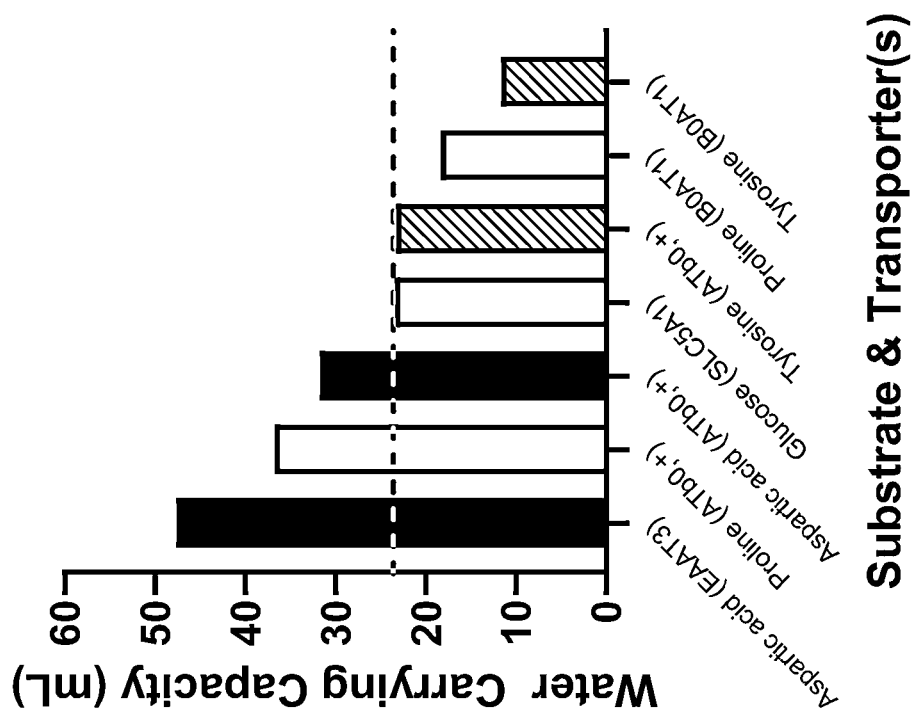
FIG. 6 is a bar graph depicting water carrying capacity of six (6) amino acids via associated transporter(s) relative to the water carrying capacity of glucose via an associated transporter.

FIG. 6 is a bar graph depicting water carrying capacity of six (6) amino acids via associated transporter(s) relative to the water carrying capacity of glucose via an associated transporter.

Figure 7:
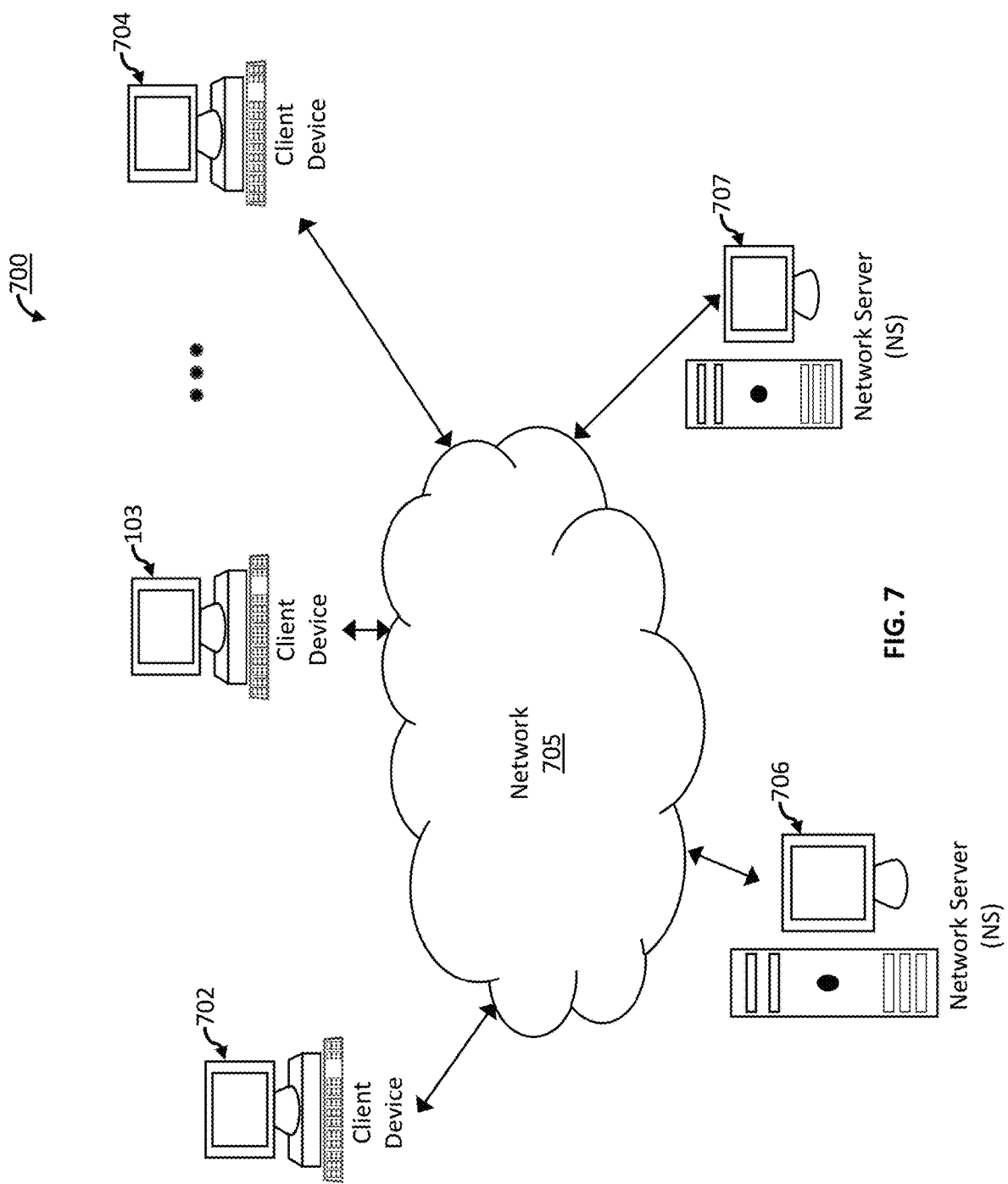
FIG. 7 depicts a block diagram of an exemplary computer-based system and platform 700 in accordance with one or more embodiments of the present disclosure.

FIG. 7 depicts a block diagram of an exemplary computer-based system and platform 700 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 700 may be configured to manage a large number of members and concurrent transactions, as detailed herein. In some embodiments, the exemplary computer-based system and platform 700 may be based on a scalable computer and network architecture that incorporates varies strategies for assessing the data, caching, searching, and/or database connection pooling. An example of the scalable architecture may be an architecture that may be capable of operate multiple servers.

In some embodiments, referring to FIG. 7, client device 702, client device 703 through client device 704 (e.g., clients) of the exemplary computer-based system and platform 700 may include virtually any computing device capable of receiving and sending a message over a network (e.g., cloud network), such as network 705, to and from another computing device, such as servers 706 and 707, each other, and the like. In some embodiments, the client devices 702 through 704 may be personal computers, multiprocessor systems, microprocessor-based or programmable consumer electronics, network PCs, and the like. In some embodiments, one or more client devices within client devices 702 through 704 may include computing devices that typically connect using a wireless communications medium such as cell phones, smart phones, pagers, walkie talkies, radio frequency (RF) devices, infrared (IR) devices, citizens band radio, integrated devices combining one or more of the preceding devices, or virtually any mobile computing device, and the like. In some embodiments, one or more client devices within client devices 702 through 704 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that may be equipped to communicate over a wired and/or wireless communication medium (e.g., NFC, RFID, NBIOT, 3G, 4G, 5G, GSM, GPRS, WiFi, WiMax, CDMA, OFDM, OFDMA, LTE, satellite, ZigBee, etc.). In some embodiments, one or more client devices within client devices 702 through 704 may include may run one or more applications, such as Internet browsers, mobile applications, voice calls, video games, videoconferencing, and email, among others. In some embodiments, one or more client devices within client devices 702 through 704 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a client device within client devices 702 through 704 may be specifically programmed by either Java, Net, QT, C, C++, Python, PHP and/or other suitable programming language. In some embodiment of the device software, device control may be distributed between multiple standalone applications. In some embodiments, software components/applications may be updated and redeployed remotely as individual units or as a full software suite. In some embodiments, a client device may periodically report status or send alerts over text or email. In some embodiments, a client device may contain a data recorder which may be remotely downloadable by the user using network protocols such as FTP, SSH, or other file transfer mechanisms. In some embodiments, a client device may provide several levels of user interface, for example, advance user, standard user. In some embodiments, one or more client devices within client devices 702 through 704 may be specifically programmed include or execute an application to perform a variety of possible tasks, such as, without limitation, messaging functionality, browsing, searching, playing, streaming, or displaying various forms of content, including locally stored or uploaded messages, images and/or video, and/or games.

In some embodiments, the exemplary network 705 may provide network access, data transport and/or other services to any computing device coupled to it. In some embodiments, the exemplary network 705 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 705 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 705 may include and implement, as an alternative or in conjunction with one or more of the above, a WiMAX architecture defined by the WiMAX forum. In some embodiments and, optionally, in combination of any embodiment described above or below, the exemplary network 705 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 705 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, OFDM, OFDMA, LTE, satellite and any combination thereof. In some embodiments, the exemplary network 705 may also include mass storage, such as network attached storage (NAS), a storage area network (SAN), a content delivery network (CDN) or other forms of computer or machine-readable media.

In some embodiments, the exemplary server 706 or the exemplary server 707 may be a web server (or a series of servers) running a network operate system, examples of which may include but are not limited to Apache on Linux or Microsoft IIS (Internet Information Services). In some embodiments, the exemplary server 706 or the exemplary server 707 may be used for and/or provide cloud and/or network computing. Although not shown in FIG. 7, in some embodiments, the exemplary server 706 or the exemplary server 707 may have connections to external systems like email, SMS messaging, text messaging, ad content providers, etc. Any of the features of the exemplary server 706 may be also implemented in the exemplary server 707 and vice versa.

In some embodiments, one or more of the exemplary servers 706 and 707 may be specifically programmed to perform, in non-limiting example, as authentication servers, search servers, email servers, social networking services servers, Short Message Service (SMS) servers, Instant Messaging (IM) servers, Multimedia Messaging Service (MMS) servers, exchange servers, photo-sharing services servers, advertisement providing servers, financial/banking-related services servers, travel services servers, or any similarly suitable service-base servers for users of the client devices 701 through 704.

In some embodiments and, optionally, in combination of any embodiment described above or below, for example, one or more exemplary computing client devices 702 through 704, the exemplary server 706, and/or the exemplary server 707 may include a specifically programmed software module that may be configured to send, process, and receive information using a scripting language, a remote procedure call, an email, a tweet, Short Message Service (SMS), Multimedia Message Service (MMS), instant messaging (IM), an application programming interface, Simple Object Access Protocol (SOAP) methods, Common Object Request Broker Architecture (CORBA), HTTP (Hypertext Transfer Protocol), REST (Representational State Transfer), SOAP (Simple Object Transfer Protocol), MLLP (Minimum Lower Layer Protocol), or any combination thereof.

Figure 8:
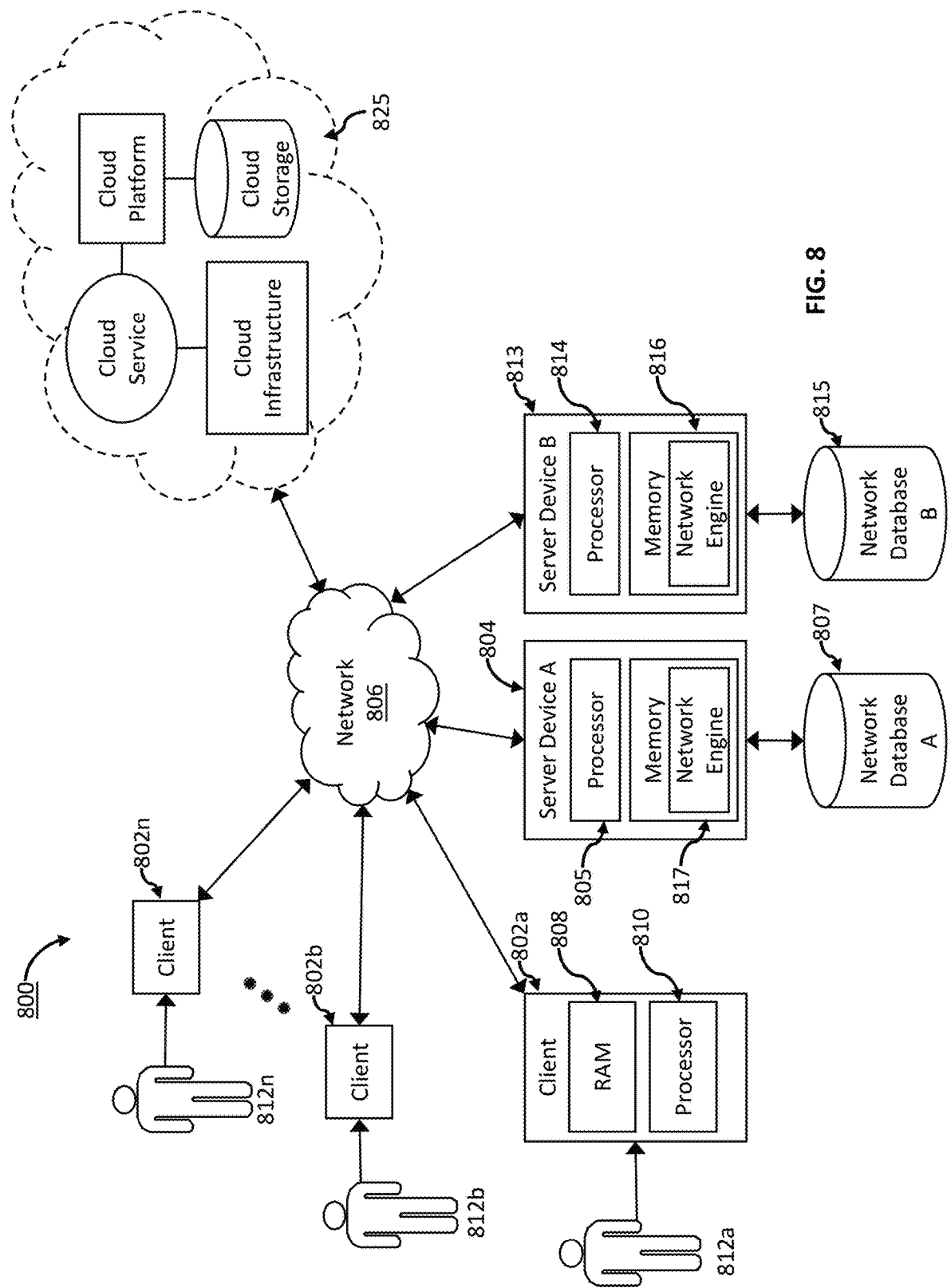
FIG. 8 depicts a block diagram of another exemplary computer-based system and platform 800 in accordance with one or more embodiments of the present disclosure.

FIG. 8 depicts a block diagram of another exemplary computer-based system and platform 800 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the client device 802a, client device 802b through client device 802n shown each at least includes a computer-readable medium, such as a random-access memory (RAM) 808 coupled to a processor 810 or FLASH memory. In some embodiments, the processor 810 may execute computer-executable program instructions stored in memory 808. In some embodiments, the processor 810 may include a microprocessor, an ASIC, and/or a state machine. In some embodiments, the processor 810 may include, or may be in communication with, media, for example computer-readable media, which stores instructions that, when executed by the processor 810, may cause the processor 810 to perform one or more steps described herein. In some embodiments, examples of computer-readable media may include, but are not limited to, an electronic, optical, magnetic, or other storage or transmission device capable of providing a processor, such as the processor 810 of client device 802a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape, or other magnetic media, or any other medium from which a computer processor may read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, client devices 802a through 802n may also comprise a number of external or internal devices such as a mouse, a CD-ROM, DVD, a physical or virtual keyboard, a display, or other input or output devices. In some embodiments, examples of client devices 802a through 802n (e.g., clients) may be any type of processor-based platforms that are connected to a network 806 such as, without limitation, personal computers, digital assistants, personal digital assistants, smart phones, pagers, digital tablets, laptop computers, Internet appliances, and other processor-based devices. In some embodiments, client devices 802a through 802n may be specifically programmed with one or more application programs in accordance with one or more principles/methodologies detailed herein. In some embodiments, client devices 802a through 802n may operate on any operate system capable of supporting a browser or browser-enabled application, such as Microsoft™, Windows™, and/or Linux. In some embodiments, client devices 802a through 802n shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 802a through 802n, user 812a, user 812b through user 812n, may communicate over the exemplary network 806 with each other and/or with other systems and/or devices coupled to the network 806. As shown in FIG. 8, exemplary server devices 804 and 813 may include processor 805 and processor 814, respectively, as well as memory 817 and memory 816, respectively. In some embodiments, the server devices 804 and 813 may be also coupled to the network 806. In some embodiments, one or more client devices 802a through 802n may be mobile clients.

In some embodiments, at least one database of exemplary databases 807 and 815 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that may be stored.

Figure 9:
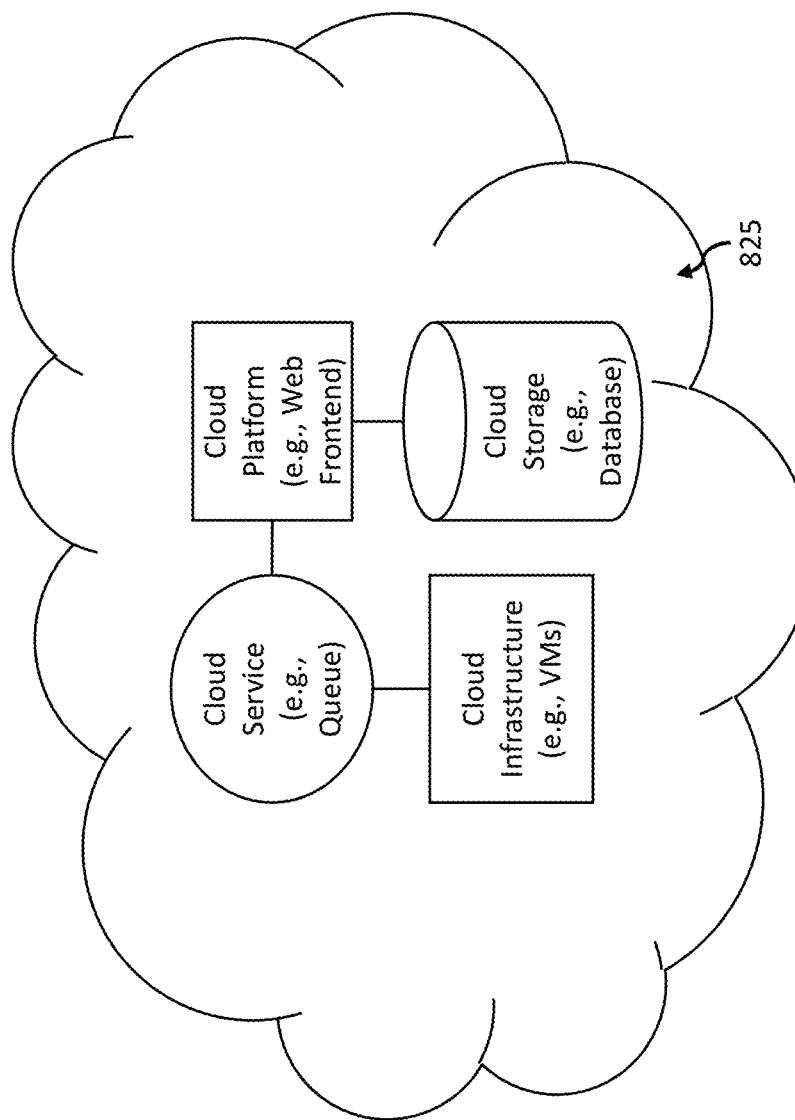
FIG. 9 illustrate schematics of an exemplary implementation of the cloud computing/architecture(s) in which the formulation optimization system 100 of the present disclosure may be specifically configured to operate.
Figure 10:
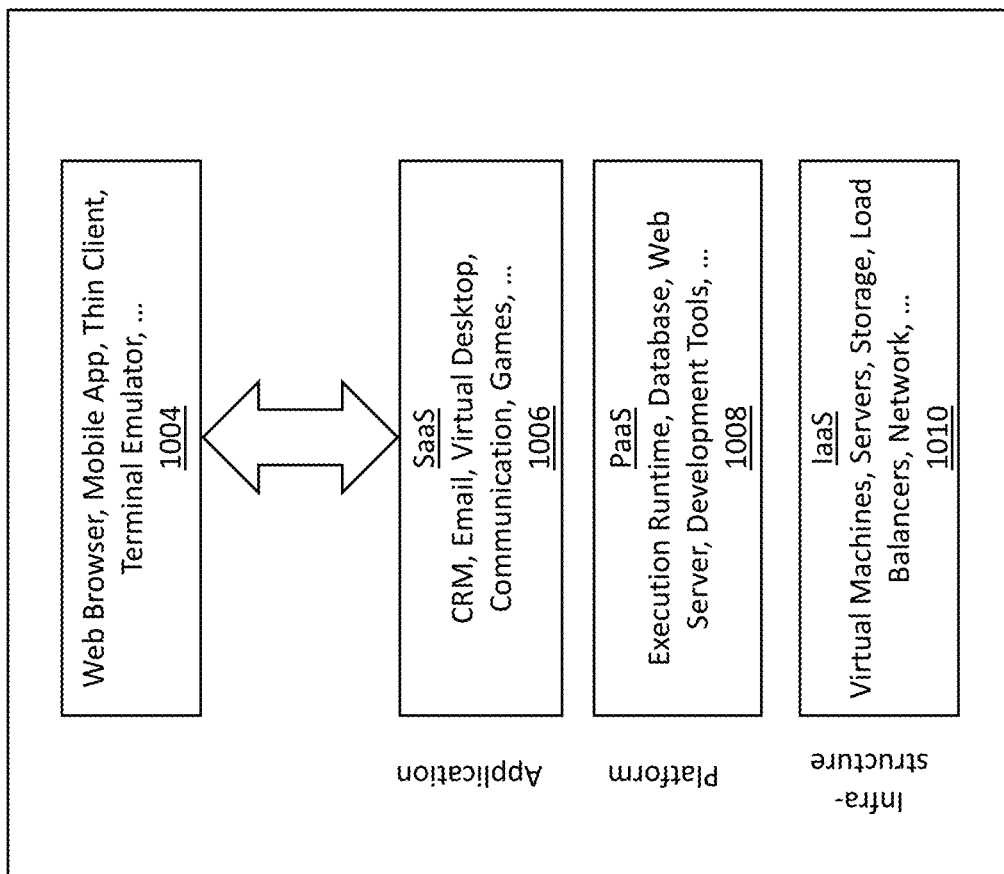
FIG. 10 illustrate schematics of an exemplary implementation of the cloud computing/architecture(s) in which the formulation optimization system 100 of the present disclosure may be specifically configured to operate.

In some embodiments, the exemplary inventive computer-based systems/platforms, the exemplary inventive computer-based devices, and/or the exemplary inventive computer-based components of the present disclosure may be specifically configured to operate in a cloud computing/architecture 825 such as, but not limiting to: infrastructure a service (IaaS) 1010, platform as a service (PaaS) 1008, and/or software as a service (SaaS) 1006 using a web browser, mobile app, thin client, terminal emulator or other endpoint 1004. FIGS. 9 and 10 illustrate schematics of exemplary implementations of the cloud computing/architecture(s) in which the formulation optimization system 100 of the present disclosure may be specifically configured to operate.

It is understood that at least one aspect/functionality of various embodiments described herein may be performed in real-time and/or dynamically. As used herein, the term "real-time" is directed to an event/action that may occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation may be used in guiding the physical process.

As used herein, the term "dynamically" and term "automatically," and their logical and/or linguistic relatives and/or derivatives, mean that certain events and/or actions may be triggered and/or occur without any human intervention. In some embodiments, events and/or actions in accordance with the present disclosure may be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes.

In some embodiments, the NFC may represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC may involve an initiator and a target; the initiator actively generates an RF field that may power a passive target. In some embodiment, this may enable NFC targets to take very simple form factors such as tags, stickers, key fobs, or cards that do not require batteries. In some embodiments, the NFC's peer-to-peer communication may be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical, or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operate system software, middleware, firmware, software modules, routines, subroutines, functions, methods, procedures, software interfaces, application program interfaces (API), instruction sets, computer code, computer code segments, words, values, symbols, or any combination thereof.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, term "server" should be understood to refer to a service point which provides processing, database, and communication facilities. By way of example, and not limitation, the term "server" may refer to a single, physical processor with associated communications and data storage and database facilities, or it may refer to a networked or clustered complex of processors and associated network and storage devices, as well as operate software and one or more database systems and application software that support the services provided by the server. Cloud servers are examples.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that may be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) FreeBSD, NetBSD, OpenBSD; (2) Linux; (3) Microsoft Windows™; (4) OpenVMS™; (5) OS X (MacOS™); (6) UNIX™; (7) Android; (8) iOS™; (9) Embedded Linux; (10) Tizen™; (11) WebOS™; (12) Adobe AIR™; (13) Binary Runtime Environment for Wireless (BREW™); (14) Cocoa™ (API); (15) Cocoa™ Touch; (16) Java™ Platforms; (17) JavaFX™; (18) QNX™; (19) Mono; (20) Google Blink; (21) Apple WebKit; (22) Mozilla Gecko™; (23) Mozilla XUL; (24) NET Framework; (25) Silverlight™; (26) Open Web Platform; (27) Oracle Database; (28) Qt™; (29) SAP NetWeaver™; (30) Smartface™; (31) Vexi™; (32) Kubernetes™ and (33) Windows Runtime (WinRT™) or other suitable computer platforms or any combination thereof. In some embodiments, illustrative computer-based systems or platforms of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments, illustrative computer-based systems or platforms of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the term "mobile electronic device," or the like, may refer to any portable electronic device that may or may not be enabled with location tracking functionality (e.g., MAC address, Internet Protocol (IP) address, or the like). For example, a mobile electronic device may include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that may be used to provide a location of, for example, a particular computing device, system or platform of the present disclosure and any associated computing devices, based at least in part on one or more of the following techniques and devices, without limitation: accelerometer(s), gyroscope(s), Global Positioning Systems (GPS); GPS accessed using Bluetooth™; GPS accessed using any reasonable form of wireless and non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink- Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTRO, SHA-1, SHA-2, Tiger (TTH), WHIRLPOOL, RNGs).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" may refer to a person who receives data provided by the data or service provider over the Internet in a browser session or may refer to an automated software application which receives the data and stores or processes the data.

The aforementioned examples are, of course, illustrative, and not restrictive.

At least some aspects of the present disclosure will now be described with reference to the following numbered clauses.

Clause 1. A method may include at least: receiving, by a processor, an amino acid formulation request for an amino acid combination for a hydration beverage; where the amino acid formulation request includes a first set of optimization criteria including: a first value of a water uptake metric, the first value being for glucose, a taste profile metric associated with a score indicative of an effect on a taste profile of the hydration beverage, accessing, by the processor, a second set of optimization criteria, including: an expression pattern for at least one associated receptor in the intestine; a second value of the water uptake metric, the second value being for the amino acid formulation, amino acid data including: a plurality of amino acid fixed properties of each amino acid of a plurality of amino acids, where the fixed properties include: an average stoichiometry for each amino acid, and a molecular weight for each amino acid; a plurality of amino acid variable characteristics of each amino acid of a plurality of amino acids, where the variable characteristics include: a molar concentration for each amino acid; generating, by the processor, an optimized amino acid-based formulation including a combination of the one or more amino acids and a concentration of the one or more amino acids by: utilizing a hydration optimization engine to optimize: the combination of one or more amino acids of the plurality of amino acids and the concentration of the one or more amino acids of the plurality of amino acids; where the hydration optimization engine may be configured to optimize based at least in part on: the first set of optimization criteria, and the second set of optimization criteria.

Clause 2. The method of clause 1 or any clause herein, further including: validating, via one or more experimental trials, the optimized amino acid-based formulation for the criteria to obtain validation data indicative of actual performance of the optimized amino acid-based formulation; and retraining the hydration optimization engine based at least in part on the validation data.

Clause 3. The method of clause 1 or any clause herein, further including: administering the hydration beverage having the optimized amino acid-based formulation for a treatment of a particular disease.

Clause 4. The method of clause 1 or any clause herein, where the first set of optimization criteria includes cost.

Clause 5. The method of clause 1 or any clause herein, at least some techniques described herein relate to an illustrative method, where the expression pattern includes expression levels of the at least one associated receptor in a plurality of parts of the intestine.

Clause 6. The method of clause 1 or any clause herein, where the expression pattern includes at least one receptor density and at least one receptor competition metric for the at least one associated receptor.

Clause 7. The method of clause 1 or any clause herein, where the first set of optimization criteria further includes a total cost associated with the amino acid combination.

Clause 8. The method of clause 1 or any clause herein, where the amino acid data further includes a cost associated with each amino acid of the plurality of amino acids.

Clause 9. The method of clause 1 or any clause herein, where the cost of each amino acid includes a cost-per-gram.

Clause 10. The method of clause 1 or any clause herein, where the amino acid data further includes a taste profile effect metric associated with each amino acid; and where taste profile effect metric includes a sub-score indicative of an individual effect on the taste profile of the hydration beverage of each amino acid.

Clause 11. A system includes at least: a processor in communication with at least one non-transitory computer readable medium storing software instructions, where the processor may be configured, upon execution of the software instructions, to: receiving, by a processor, an amino acid formulation request for an amino acid combination for a hydration beverage; where the amino acid formulation request includes a first set of optimization criteria: a first value of a water uptake metric, the first value being for glucose, a taste profile metric associated with a score indicative of an effect on a taste profile of the hydration beverage, access a second set of optimization criteria, including: an expression pattern for at least one associated receptor in the intestine; a second value of the water uptake metric, the second value being for the amino acid formulation, amino acid data including a plurality of amino acid characteristics of each amino acid of a plurality of amino acids, where the amino acid data includes: an average stoichiometry for each amino acid, a molecular weight for each amino acid, or a molar concentration for each amino acid; generate an optimized amino acid-based formulation including a combination of the one or more amino acids and a concentration of the one or more amino acids by: utilizing a hydration beverage optimization engine to optimize: the combination of one or more amino acids of the plurality of amino acids and the concentration of the one or more amino acids of the plurality of amino acids; where the hydration beverage optimization engine may be configured to optimize based at least in part on: the first set of optimization criteria, and the second set of optimization criteria.

Clause 12. The system of clause 11, or any clause herein, where the processor may be further configured to: validating, via one or more experimental trials, the optimized amino acid-based formulation for the criteria.

Clause 13. The system of clause 11, or any clause herein, where the processor may be further configured to: administering the hydration beverage having the optimized amino acid-based formulation for a treatment of a particular disease.

Clause 14. The system of clause 11, or any clause herein, where the first set of optimization criteria includes cost.

Clause 15. The system of clause 11, or any clause herein, where the expression pattern includes expression levels of the at least one associated receptor in the intestine.

Clause 16. The system of clause 11, or any clause herein, where the expression pattern includes at least one receptor density and at least one receptor competition metric for the at least one associated receptor.

Clause 17. The system of clause 11, or any clause herein, where the first set of optimization criteria further includes a total cost associated with the amino acid combination.

Clause 18. The system of clause 11, or any clause herein, where the amino acid data further includes a cost associated with each amino acid of the plurality of amino acids.

Clause 19. The system of clause 11, or any clause herein, where the cost of each amino acid includes a cost-per-gram.

Clause 20. The system of clause 11, or any clause herein, where the amino acid data further includes a taste profile effect metric associated with each amino acid; and where taste profile effect metric includes a sub-score indicative of an individual effect on the taste profile of the hydration beverage of each amino acid.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein may be utilized in any combination with each other. Further still, the various steps may be carried out in any desired order (and any desired steps may be added and/or any desired steps may be eliminated).

The invention claimed is:

1. A method of manufacturing a beverage formulation comprising:
obtaining, by at least one processor, the beverage formulation comprising an optimized amino acid-based combination by:
determining
a first set of optimization criteria comprising:
a first value of a water uptake metric, the first value being for glucose,
a taste profile metric associated with a score indicative of an effect on a taste profile of the hydration beverage;
determining a second set of optimization criteria, comprising:
an expression pattern for at least one associated receptor in the intestine;
a second value of the water uptake metric, the second value being for the amino acid formulation;
amino acid data comprising:
a plurality of amino acid fixed properties of each amino acid of a plurality of amino acids, wherein the fixed properties comprise:
an average stoichiometry for each amino acid, and
a molecular weight for each amino acid;
a plurality of amino acid variable characteristics of each amino acid of the plurality of amino acids, wherein the variable characteristics comprise:
a molar concentration for each amino acid;
iteratively simulating a plurality of amino acid-based combination simulations, each amino acid-based combination simulation simulating the second value of the water uptake metric for a candidate amino acid-based combination of a plurality of candidate amino acid-based combinations based at least in part on transport kinetics modelling of each candidate amino acid-based combination to obtain the optimized amino acid-based combination comprising a plurality of selected amino acids having at least one concentration;
wherein each candidate amino acid-based combination comprises a combination of a plurality of candidate amino acids and a concentration of the plurality of candidate amino acids;
wherein the plurality of amino acid-based combination simulations is configured to optimize:
the combination of the one or more candidate amino acids of the plurality of amino acids so as to obtain the plurality of selected amino acids and
the concentration of the one or more candidate amino acids of the plurality of amino acids so as to obtain the at least one concentration of the plurality of selected amino acids;
wherein the plurality of amino acid-based combination simulations is configured to optimize based at least in part on:
the first set of optimization criteria, and
the second set of optimization criteria; and
automatically sending, by the at least one processor, a control signal to production equipment at a manufacturing facility to dispense the plurality of selected amino acids having at least one concentration to produce the beverage formulation.

2. The method of claim 1, further comprising:
validating, via one or more experimental trials, the optimized amino acid-based combination for the criteria to obtain validation data indicative of actual performance of the optimized amino acid-based combination; and
retraining the hydration optimization engine based at least in part on the validation data.

3. The method of claim 1, further comprising:
administering the hydration beverage having the optimized amino acid-based combination for a treatment of a particular disease.

4. The method of claim 1, wherein the first set of optimization criteria comprises cost and the amino acid data further comprises a cost associated with each amino acid of the plurality of amino acids.

5. The method of claim 1, wherein the expression pattern comprises expression levels of the at least one associated receptor in a plurality of parts of the intestine.

6. The method of claim 5, wherein the expression pattern comprises at least one receptor density and at least one receptor competition metric for the at least one associated receptor.

7. The method of claim 1, wherein the amino acid data further comprises a taste profile effect metric associated with each amino acid; and
 wherein taste profile effect metric comprises a sub-score indicative of an individual effect on the taste profile of the hydration beverage of each amino acid.

8. A system for manufacturing a beverage formulation comprising:
 production equipment at a manufacturing facility; and
 at least one controller at the manufacturing facility configured to:
  obtain the beverage formulation comprising an optimized amino acid-based combination by:
   determining
    a first set of optimization criteria comprising:
     a first value of a water uptake metric, the first value being for glucose,
     a taste profile metric associated with a score indicative of an effect on a taste profile of the hydration beverage,
    determining a second set of optimization criteria, comprising:
     an expression pattern for at least one associated receptor in the intestine;
     a second value of the water uptake metric, the second value being for the amino acid formulation;
    amino acid data comprising:
     a plurality of amino acid fixed properties of each amino acid of a plurality of amino acids, wherein the fixed properties comprise:
      an average stoichiometry for each amino acid, and
      a molecular weight for each amino acid;
     a plurality of amino acid variable characteristics of each amino acid of the plurality of amino acids, wherein the variable characteristics comprise:
      a molar concentration for each amino acid;
   iteratively simulating a plurality of amino acid-based combination simulations, each amino acid-based combination simulation simulating the second value of the water uptake metric for a candidate amino acid-based combination of a plurality of candidate amino acid-based combinations based at least in part on transport kinetics modelling of each candidate amino acid-based combination to obtain the optimized amino acid-based combination comprising a plurality of selected amino acids having at least one concentration;
    wherein each candidate amino acid-based combination comprises a combination of a plurality of candidate amino acids and a concentration of the plurality of candidate amino acids;
    wherein the plurality of amino acid-based combination simulations is configured to optimize:
     the combination of the one or more candidate amino acids of the plurality of amino acids so as to obtain the plurality of selected amino acids and
     the concentration of the one or more candidate amino acids of the plurality of amino acids so as to obtain the at least one concentration of the plurality of selected amino acids;
    wherein the plurality of amino acid-based combination simulations is configured to optimize based at least in part on:
     the first set of optimization criteria, and
     the second set of optimization criteria; and
  automatically send a control signal to the production equipment to dispense the plurality of selected amino acids having at least one concentration to produce the beverage formulation.

9. The system of claim 8, wherein the controller is further configured to:
 validating, via one or more experimental trials, the optimized amino acid-based combination for the criteria.

10. The system of claim 8, wherein the controller is further configured to:
 administering the hydration beverage having the optimized amino acid-based combination for a treatment of a particular disease.

11. The system of claim 8, wherein the first set of optimization criteria comprises cost and the amino acid data further comprises a cost associated with each amino acid of the plurality of amino acids.

12. The system of claim 8, wherein the expression pattern comprises expression levels of the at least one associated receptor in the intestine.

13. The system of claim 12, wherein the expression pattern comprises at least one receptor density and at least one receptor competition metric for the at least one associated receptor.

14. The system of claim 8, wherein the amino acid data further comprises a taste profile effect metric associated with each amino acid; and
 wherein taste profile effect metric comprises a sub-score indicative of an individual effect on the taste profile of the hydration beverage of each amino acid.

15. The system of claim 12, wherein the expression pattern comprises at least one receptor density and at least one receptor competition metric for the at least one associated receptor.

16. A method of manufacturing a beverage formulation comprising:
 receiving, by at least one processor, the beverage formulation comprising an optimized amino acid-based combination;
 wherein the optimized amino acid-based combination has been determined by:
  determining a first set of optimization criteria comprising:
   a first value of a water uptake metric, the first value being for glucose,
   a taste profile metric associated with a score indicative of an effect on a taste profile of the hydration beverage;
  determining a second set of optimization criteria, comprising:
   an expression pattern for at least one associated receptor in the intestine;

a second value of the water uptake metric, the
second value being for the amino acid formulation;
amino acid data comprising:
a plurality of amino acid fixed properties of
each amino acid of a plurality of amino acids,
wherein the fixed properties comprise:
an average stoichiometry for each amino acid,
and
a molecular weight for each amino acid;
a plurality of amino acid variable characteristics
of each amino acid of the plurality of amino
acids, wherein the variable characteristics comprise:
a molar concentration for each amino acid;
iteratively simulating a plurality of amino acid-based
combination simulations, each amino acid-based
combination simulation simulating the second
value of the water uptake metric for a candidate
amino acid-based combination of a plurality of
candidate amino acid-based combinations based at
least in part on transport kinetics modelling of
each candidate amino acid-based combination to
obtain the optimized amino acid-based combination comprising a plurality of selected amino acids
having at least one concentration;
wherein each candidate amino acid-based combination comprises a combination of a plurality of
candidate amino acids and a concentration of
the plurality of candidate amino acids;
wherein the plurality of amino acid-based combination simulations are configured to optimize:
the combination of the one or more candidate
amino acids of the plurality of amino acids so as
to obtain the plurality of selected amino acids
the concentration of the one or more candidate
amino acids of the plurality of amino acids so as
to obtain the at least one concentration of the
plurality of selected amino acids;
wherein the plurality of amino acid-based combination simulations are configured to optimize
based at least in part on:
the first set of optimization criteria, and
the second set of optimization criteria; and
automatically sending, by the at least one processor, a
control signal to production equipment at a manufacturing facility to dispense the plurality of selected
amino acids having at least one concentration to produce the beverage formulation.

17. The method of claim 16, further comprising:
validating, via one or more experimental trials, the optimized amino acid-based combination for the criteria to
obtain validation data indicative of actual performance
of the optimized amino acid-based combination; and
retraining the hydration optimization engine based at least
in part on the validation data.

18. The method of claim 16, further comprising:
administering the hydration beverage having the optimized amino acid-based combination for a treatment of
a particular disease.

19. The method of claim 16, wherein the first set of
optimization criteria comprises cost and the amino acid data
further comprises a cost associated with each amino acid of
the plurality of amino acids.

20. The method of claim 16, wherein the expression
pattern comprises expression levels of the at least one
associated receptor in a plurality of parts of the intestine.

21. The method of claim 20, wherein the expression
pattern comprises at least one receptor density and at least
one receptor competition metric for the at least one associated receptor.

22. The method of claim 16, wherein the amino acid data
further comprises a taste profile effect metric associated with
each amino acid; and
wherein taste profile effect metric comprises a sub-score
indicative of an individual effect on the taste profile of
the hydration beverage of each amino acid.

23. A system for manufacturing a beverage formulation
comprising:
production equipment at a manufacturing facility; and
at least one controller at the manufacturing facility configured to:
receive the beverage formulation comprising an optimized amino acid-based combination;
wherein the optimized amino acid-based combination is obtained by:
determining a first set of optimization criteria
comprising:
a first value of a water uptake metric, the first
value being for glucose,
a taste profile metric associated with a score
indicative of an effect on a taste profile of the
hydration beverage;
determining a second set of optimization criteria,
comprising:
an expression pattern for at least one associated
receptor in the intestine;
a second value of the water uptake metric, the
second value being for the amino acid formulation;
amino acid data comprising:
a plurality of amino acid fixed properties of
each amino acid of a plurality of amino acids,
wherein the fixed properties comprise:
an average stoichiometry for each amino acid,
and
a molecular weight for each amino acid;
a plurality of amino acid variable characteristics
of each amino acid of the plurality of amino
acids,
wherein the variable characteristics comprise:
a molar concentration for each amino acid;
iteratively simulating a plurality of amino acid-based combination simulations, each amino
acid-based combination simulation simulating
the second value of the water uptake metric for
a candidate amino acid-based combination of a
plurality of candidate amino acid-based combinations based at least in part on transport kinetics modelling of each candidate amino acid-based combination to obtain the optimized
amino acid-based combination comprising a
plurality of selected amino acids having at least
one concentration;
wherein each candidate amino acid-based combination comprises a combination of a plurality
of candidate amino acids and a concentration of
the plurality of candidate amino acids;
wherein the plurality of amino acid-based combination simulations is configured to optimize:
the combination of the one or more candidate
amino acids of the plurality of amino acids so as
to obtain the plurality of selected amino acids
and the concentration of the one or more candidate amino acids of the plurality of amino acids so as to obtain the at least one concentration of the plurality of selected amino acids;
wherein the plurality of amino acid-based combination simulations is configured to optimize based at least in part on:
the first set of optimization criteria, and
the second set of optimization criteria; and
automatically send a control signal to production equipment at a manufacturing facility to dispense the plurality of selected amino acids having at least one concentration to produce the beverage formulation.

24. The system of claim 23, wherein the controller is further configured to:
validating, via one or more experimental trials, the optimized amino acid-based combination for the criteria.

25. The system of claim 24, wherein the controller is further configured to:
administering the hydration beverage having the optimized amino acid-based combination for a treatment of a particular disease.

26. The system of claim 24, wherein the first set of optimization criteria comprises cost and the amino acid data further comprises a cost associated with each amino acid of the plurality of amino acids.

27. The system of claim 24, wherein the expression pattern comprises expression levels of the at least one associated receptor in the intestine.

28. The system of claim 24, wherein the amino acid data further comprises a taste profile effect metric associated with each amino acid; and
wherein taste profile effect metric comprises a sub-score indicative of an individual effect on the taste profile of the hydration beverage of each amino acid.

* * * * *